(12) United States Patent
Lockhart

(10) Patent No.: US 8,399,525 B2
(45) Date of Patent: Mar. 19, 2013

(54) TREATMENT OF GAUCHER DISEASE WITH SPECIFIC PHARMACOLOGICAL CHAPERONES AND MONITORING TREATMENT USING SURROGATE MARKERS

(75) Inventor: David J. Lockhart, Del Mar, CA (US)

(73) Assignee: Amicus Therapeutics, Inc., Cranbury, NJ (US)

(*) Notice: Subject to any disclaimer, the term of this patent is extended or adjusted under 35 U.S.C. 154(b) by 356 days.

(21) Appl. No.: 12/595,071

(22) PCT Filed: Apr. 11, 2008

(86) PCT No.: PCT/US2008/060116
§ 371 (c)(1),
(2), (4) Date: Mar. 18, 2010

(87) PCT Pub. No.: WO2008/128106
PCT Pub. Date: Oct. 23, 2008

(65) Prior Publication Data
US 2010/0196279 A1 Aug. 5, 2010

Related U.S. Application Data

(60) Provisional application No. 60/911,699, filed on Apr. 13, 2007, provisional application No. 61/028,123, filed on Feb. 12, 2008.

(51) Int. Cl.
*C12Q 1/00* (2006.01)
*A61K 47/00* (2006.01)

(52) U.S. Cl. ............................... 514/789; 435/4

(58) Field of Classification Search ........................ None
See application file for complete search history.

(56) References Cited

U.S. PATENT DOCUMENTS
2005/0113415 A1* 5/2005 Fan et al. ...................... 514/317
2006/0287358 A1 12/2006 Wustman

FOREIGN PATENT DOCUMENTS
WO 2005046611 A2 5/2005

OTHER PUBLICATIONS

Fiore et al. (J Bone Miner Metab (2002) 20: 34-38).*
Cabrera-Salazar et al. (Clinica Chimica Acta 344 (2004): 101-107).*
Deegan et al. (Acta Paediatr Suppl. Mar. 2005;94(447): 47-50, abstract only).*
Aerts et al. (Acta Paediatr Suppl. Mar. 2005;94(447): 43-6, abstract only).*
Breemen et al. (Biochimica et Biophysica Acta 1772 (2007) 788-796).*
International Search Report for PCT/US08/060116, dated Jul. 3, 2008.
International Preliminary Report on Patentability for International Application No. PCT/US2008/060116, dated Oct. 13, 2009.
Steet, R. A. et al., "The iminosugar isofagomine increase the activity of N370S mutant acid beta-glucosidase in Gaucher fibroblasts by several mechanisms", Proc. Natl. Acad. Sci. USA, vol. 103, No. 37, p. 13813-13818 (Sep. 12, 2006).
Chang, H. H. et al., "Hydrophilic iminosugar active-site-specific chaperons increase residual glucocerebrosidase activity in fibroblasts from Gaucher patients", FEBS J., vol. 273, No. 17, p. 4082-4092 (Sep. 2006).
Lieberman, R. L. et al., Structure of beta-glucosidase with pharmacological chaperone provides insight into Gaucher disease, Nat. Chem. Biol., vol. 3, No. 2, p. 101-107 (Feb. 2007).
Boot, Rolf G et al: "Marked elevation of the chemokine CCL18/PARC in Gaucher disease: a novel surrogate marker for assessing therapeutic intervention." Blood Jan. 1, 2004, vol. 103, No. 1, Jan. 1, 2004, pp. 33-39, XP002572037 ISSN: 0006-4971.
Yu, L et al: "alpha-1-C-Octyl-1-deoxynojirimycin as a pharmacological chaperone for Gaucher disease" Bioorganic & Medicinal Chemistry, Pergamon, GB, vol. 14, No. 23, Dec. 1, 2006, pp. 7736-7744, XP025132835 ISSN: 0968-0896 [retrieved on Dec. 1, 2006].
Weinreb, Neal J et al: "Pharmacological chaperone therapy for the treatment of Gaucher disease: Results of phase 1 clinical trials and a clinical ex vivo response study with a survey of blood markers for 53 Gaucher patients" Blood, American Society of Hematology, US, vol. 110, No. 11, Part 1, Nov. 1, 2007, p. 709A, XP009130375 ISSN: 0006-4971.
Supplementary European Search Report issued for European Patent Application No./Patent No. 08745676.0-2404/2139323, dated Mar. 22, 2010.

* cited by examiner

*Primary Examiner* — Suzanne M Noakes
*Assistant Examiner* — Jae W Lee
(74) *Attorney, Agent, or Firm* — SorinRand LLP

(57) ABSTRACT

Provided is a method of monitoring the treatment of Gaucher disease with specific pharmacological chaperones using systemic and/or cellular surrogate markers. Also provided is a new biomarker that may be used to monitor the progress of such treatment.

4 Claims, 12 Drawing Sheets

Isofagomine Treatment on Gba Activity in Various Tissues

Isofagomine Treatment on Chitotriosidase Activity of L444P mice

Isofagomine Effects on Serum Parameters

TREATMENT OF GAUCHER DISEASE WITH SPECIFIC PHARMACOLOGICAL CHAPERONES AND MONITORING TREATMENT USING SURROGATE MARKERS

CROSS-REFERENCE TO RELATED APPLICATIONS

This application is a National Phase Application of PCT/US2008/060116 filed on Apr. 11, 2008, which claims priority to U.S. Provisional Application Ser. No. 60/911,699, filed Apr. 13, 2007; and to U.S. Provisional Application Ser. No. 61/028,123, filed Feb. 12, 2008, both of which are hereby incorporated by reference in their entireties herein.

FIELD OF THE INVENTION

The present invention provides a method for monitoring the treatment of an individual having Gaucher disease with a specific pharmacological chaperone by determining the presence and levels of specific surrogate markers such as glucocerebrosidase, glucosylceramide, chitotriosidase, inflammatory cytokines and chemokines, glucosylceramide-containing macrophages, makers of bone metabolism, and α-synuclein. The present invention also provides a method for monitoring the treatment of an individual having Gaucher disease with a specific pharmacological chaperone by evaluating the effects of treatment at the cellular level.

BACKGROUND

Gaucher Disease

Gaucher disease is a lysosomal storage disorder that is associated with the accumulation of glycosphingolipids (GSL) in cells, particularly monocytes and macrophages, of afflicted individuals. This aberrant build up of GSL results from a genetic deficiency (mutation) in the lysosomal enzyme acid β-glucosidase (GCase; glucocerebrosidase), the lysosomal hydrolase that breaks down the GSL glucosylceramide (GluCer). The majority of Gba mutations cause GCase protein to misfold in the endoplasmic reticulum (ER). Misfolded GCase is recognized by the ER quality control system and subsequently degraded instead of being processed and trafficking to the lysosome (Street et al., Proc Natl Acad Sci USA 2006; vol. 103; no. 37: 13813-18).

Gaucher disease is pan-ethnic, with an overall disease frequency of about 1 in 50,000-100,000 births. Certain populations have a higher prevalence of Gaucher disease. In the Ashkenazi Jewish population, for example, about 1 in 15 people are carriers for a Gba mutation (Aharon-Peretz et al., New Eng. J. Med. 2004; 351: 1972-77). According to the National Gaucher Foundation, about 2,500 Americans suffer from Gaucher disease.

Gaucher disease is an autosomal recessive disorder and is the most common lysosomal storage disease. The disease has been classified into three clinical types, depending on neurological involvement and disease severity (Cox et al., Q J Med. 2001; 94: 399-402). Type 1 is the most common and is characterized by an absence of neurological involvement. Type 1 patients exhibit a broad spectrum of severity, and some can remain asymptomatic throughout life. Most Type 1 patients exhibit enlargement of the spleen and liver, skeletal abnormalities and bone lesions, and sustained inflammatory reactions. Hepatic glucocerebroside levels are elevated from 23-fold to 389-fold above normal levels in Type I Gaucher patients.

Type 2 Gaucher disease is the rarest, most severe form, and is associated with early onset of acute neurologic disease. The characteristic feature of neuronopathic Gaucher disease is an abnormality of horizontal gaze. Afflicted patients develop progressive encephalopathy and extrapyramidal symptoms such as rigidity and Parkinson's-like movement (parkinsonism). Most Type 2 Gaucher patients die in early childhood from apnea or aspiration due to neurological deterioration.

Type 3 Gaucher disease also has neurological involvement, although to a lesser extent than Type 2. Type 3 patients also have the hepatosplenomegaly and skeletal defects characteristic of Type 1, and central nervous system symptoms that include poor coordination of movements (ataxia), seizures, paralysis of the eye muscles, epilepsy, and dementia. People with Type 3 Gaucher disease can live into adulthood, but may have a shortened life span. Three sub-classifications of Type 3 have been reported: Type 3a, which is associated with prominent hepatosplenomegaly and bone marrow disease; Type 3b, which is associated with limited systemic symptoms; and Type 3c, which is associated with hepatosplenomegaly, corneal opacities, progressive ataxia and dementia, and cardiac valve and aortic root calcification.

Over 200 Gba mutations have been identified in affected Gaucher patients. Most Gaucher patients exhibit some residual GCase activity. However, a poor correlation of genotype with phenotype has plagued efforts to elucidate the molecular basis for phenotypic variation (Sidransky, Mol. Genetics and Metab. 2004; 83: 6-15). There is a lack of phenotypic consistency even among identical twins harboring the same genetic mutations. Despite this, different mutations are associated with the three disease types. The presence of point mutation N370S on at least one allele (heterozygotes) is almost universally associated with type 1 Gaucher disease (Cox, supra).

Treatment

Treatment of clinically manifested Types 1 and 3 disease is predominantly by enzyme replacement therapy (ERT) of recombinant GCase (Ceredase® and Cerezyme®, Genzyme Inc.). Bone marrow transplants (BMT) also have been employed as treatment for Gaucher disease (Types 1 and 3). Because macrophages are derived from bone marrow stem cells, allogeneic bone marrow transplantation (BMT) has been applied successfully in a small number of Gaucher patients. However, BMT can be associated with severe morbidity and mortality, and only a small fraction of patients have appropriate histocompatible donors.

A third, relatively recent approach to treating protein deficiencies involves the use of small molecule inhibitors to inhibit synthesis the natural substrate of the deficient enzyme protein, thereby ameliorating the pathology. This "substrate reduction" approach (SRT) has been specifically described for a class of about 40 related enzyme disorders called lysosomal storage disorders or glycosphingolipid storage disorders including Gaucher disease.

A fourth approach, a specific chaperone strategy, rescues mutated proteins from degradation presumably in the endoplasmic reticulum (ER) or in other cellular protein degradation/disposal systems. In particular embodiments, this strategy employs small molecule reversible inhibitors which specifically bind to a defective lysosomal enzyme associated with a particular lysosomal disorder. In the absence of therapy, the mutated enzyme folds improperly in the ER (Ishii et al., Biochem. Biophys. Res. Comm. 1996; 220: 812-815), is retarded in its maturation to a final product, and is subsequently degraded via ER associated degradation pathways. The chaperone strategy involves the use of a compound that facilitates the correct folding of a mutated protein, to prevent undue or abnormal degradation from the ER quality control system, or accumulation of misfolded protein in the cell. These specific chaperones are designated specific pharmacological chaperones (or active site-specific chaperones).

The chaperone strategy has been described and exemplified for enzymes involved in lysosomal storage disorders as in U.S. Pat. Nos. 6,274,597, 6,583,158, 6,589,964, 6,599,919, and 7,141,582, to Fan et al., which are incorporated herein by reference in their entirety. Rescue of GCase from Gaucher patient cells has been described using the imino sugar, isofagomine (IFG), and its derivatives, and using other compounds specific for GCase (described in pending U.S. patent application Ser. Nos. 10/988,428, and 10/988,427, both filed Nov. 12, 2004). Such compounds include glucoimidazole ((5R,6R,7S,8S)-5-hydroxymethyl-5,6,7,8-tetrahydroimidazo[1,2a]pyridine-6,7,8-triol).

Surrogate Markers

Despite the phenotypic inconsistency, Gaucher patients exhibit several consistent surrogate markers of the disease that are used to evaluate clinical response to treatment. The present invention relates to a method of monitoring treatment of a Gaucher patient following treatment with a specific pharmacological chaperone, by evaluating changes in at least one, and preferably multiple, surrogate markers of Gaucher disease.

SUMMARY OF THE INVENTION

The present invention provides a method for monitoring treatment of a Gaucher disease patient with a specific pharmacological chaperone for acid β-glucosidase (GCase), by evaluating changes in the presence and/or level of a surrogate marker that is associated with Gaucher disease, where an improvement indicates that the individual is responding to the chaperone therapy.

In one embodiment, the surrogate marker is a systemic surrogate marker.

Systemic surrogate markers include at least one of the following: decreased lysosomal GCase activity in cells and urine; the presence of lipid-laden macrophages ("Gaucher macrophages"); hepatosplenomagaly; increased levels of chitotriosidase; increased levels of liver enzymes; increased levels of lysosomal proteins including LAMP-1 and saposin C, increased levels of pulmonary chemokine PARC/CCL18; increased levels of plasma α-synuclein; increased levels of angiotensin converting enzyme (ACE) and total acid phosphatase; immunological defects such as anemia, thrombocytopenia, leukopenia, hypergammaglobulinemia, decreased amount of T-lymphocytes in the spleen, systemic B cell hyperproliferation, plasmacytosis, increased levels of inflammatory cytokines (TNF-α, IL-1β, IL-1α, IL-6) and chemokines including those associated with bone metabolism and multiple myeloma (TNF-α, IL-8, IL-17, MIP-1α, MIP-1β, VEGF, and TRACP 5b, BAP), the presence of inflammatory foci in tissues or organs comprising macrophages, lymphocytes, and neutrophils, and impaired neutrophil chemotaxis; skeletal defects such as infiltration of Gaucher cells in the bone marrow, lytic lesions, osteoschlerosis, osteoporosis, bone crises and bone pain, fractures, vertebral collapse, and reduced levels of triglycerides; decreased levels of bone-specific alkaline phosphatase, neurological symptoms such as neuronal loss, neurodegeneration, horizontal gaze abnormalities, myoclonic movements, corneal opacity, ataxia, dementia, spasticity; seizures, auditory impairment; cognitive impairment; and pulmonary infiltration of Gaucher macrophages and pulmonary hypertension.

In a specific embodiment, the combination of markers expected following treatment of Gaucher disease with a pharmacological chaperone are as follows: increased β-glucocerebrosidase (GCase) levels in white blood cells, skin, cerebrospinal fluid (CSF) and urine; decreased glucocerebroside (GlcCer) levels in white blood cells, plasma, serum, urine, CSF and skin; decreased α-synuclein levels in plasma and CSF; increased bone-specific alkaline phosphatase (BAP) activity in plasma; decreased tartrate-resistant acid phosphatase 5b (TRACP 5b) activity in plasma, decreased chitotriosidase activity in plasma; decreased pulmonary and activation regulated chemokine (PARC) in plasma and urine, and decreased interleukin 8, interleukin 17, VEGF MIP-1β and MIP-1α level in plasma as well as LAMP-1 and cathepsin D. Additional markers evaluated include decrease in liver and spleen volume from baseline; increase in hemoglobin level from baseline; change in hematocrit level from baseline; change in platelet count from baseline; improvement in bone mineral density from baseline; improvement in radiographic findings from baseline; decreased GM3 levels in plasma, urine, white blood cells (WBC) and CSF; decreased chitotriosidase activity in plasma and CSF, in particular IL-8, IL-6, membrane markers in CSF.

In another embodiment, the surrogate marker is a sub-cellular surrogate marker.

Sub-cellular surrogate markers include at least one of the following: aberrant trafficking of GCase in cells from Gaucher patients from the ER to the lysosome; aberrant trafficking of cellular lipids though the endosomal pathway; the presence of increased amounts misfolded GCase in the ER or cytosol; the presence of ER and/or stress resulting from toxic accumulation of GCase (as determined by gene and/or protein expression of stress-related markers); aberrant endosomal pH levels; the presence of increased plasma membrane expression of MHCII and/or CD1d on monocytes; aberrant cell morphology; suppression of the ubiquitin/proteasome pathway; and an increase in the amount of ubiquitinated proteins.

In a specific embodiment, the individual has Type 3 Gaucher disease with cardiac involvement and the surrogate marker is calcification of the aortic and/or mitral valves.

In a further embodiment, the specific pharmacological chaperone used in the therapy is an inhibitor of acid β-glucosidase, such as a reversible competitive inhibitor.

In specific embodiments, the inhibitor is isofagomine, C-benzyl-isofagomine or compounds disclosed in U.S. Pat. Nos. 6,583,158; 6,744,135; 6,599,919; 6,589,964, 6,916,829; 7,141,582; 5,844,102; 5,863,903; 6,046,214; 5,854,272; 6,541,836; 6,316,489; 6,239,163; 6,590,118 and PCT Application No. WO 04/037233 all of which are incorporated by reference.

The present invention also provides a method for treating Gaucher disease with effective amount of a specific chemical chaperone that binds to acid β-glucosidase, and monitoring its effect on cytoplasmic staining of cells, where restoration of an abnormal indicates that the individual with Gaucher disease is responding to chaperone treatment.

In one embodiment, the cytoplasmic staining is lysosomal staining, in particular, detection of acid β-glucosidase or LAMP-1 expression in the lysosome.

In another embodiment, the cytoplasmic staining is detection of polyubiquitinated proteins.

In a particular embodiment, the specific pharmacological chaperone is an inhibitor of acid β-glucosidase, such as a reversible competitive inhibitor.

In specific embodiment, the inhibitor is isofagomine, C-benzyl-isofagomine, or glucoimidazole.

BRIEF DESCRIPTION OF THE DRAWINGS

This patent application contains at least one drawing executed in color. Copies of this patent or patent application publication with color drawing(s) will be provided by the Office upon request and payment of the necessary fee.

FIG. 1 depicts GCase enhancement results from a Phase 1 multiple-ascending dose study of isofagomine tartrate in healthy volunteers.

FIG. 2A-D.

FIG. 3A-B.

FIG. 4 depicts changes in levels of chitotriosidase in a mouse model of Gaucher disease following treatment with IFG.

FIG. 5A-D.

FIG. 6 depicts a comparison of plasma α-synuclein levels from healthy volunteers and patients with Gaucher disease.

FIGS. 7A-N. FIGS. 7E-F show an overlay of dual GCase and LAMP-1 staining in Gaucher fibroblasts. Also depicted is a dual overlay (LAMP-1 and GCase) of Gaucher cells treated with the specific pharmacological chaperone isofagomine (7G-H), or C-benzyl-isofagomine (7I-J). Lastly, FIGS. 7K-N show staining of Gaucher cells for GCase only. Control Gaucher cells were stained with secondary antibody only (7K), or were not treated (7L), or were treated with isofagomine (7M), or C-benzyl-isofagomine (7N).

FIG. 8 is comparison of Gcase activity in WBCs, GlcCer concentration in WBC, chitotriosidase activity in plasma and α-synuclein levels in plasma in Gaucher Patients as compared to controls.

FIG. 9 is a comparison of TRACP 5b Activity In Plasma (Females), TRACP 5b Activity In Plasma (Males), BAP Activity in Plasma (Females) and BAP Activity in Plasma (Males) in Gaucher Patients as compared to controls.

FIG. 10 is a comparison of PARC, IL-8, MIP-1α, IL-17, VEGF, and IL-17 vs. VEGF Activity In Plasma (Femalesin Gaucher Patients as compared to controls.

DETAILED DESCRIPTION

Figure 1:
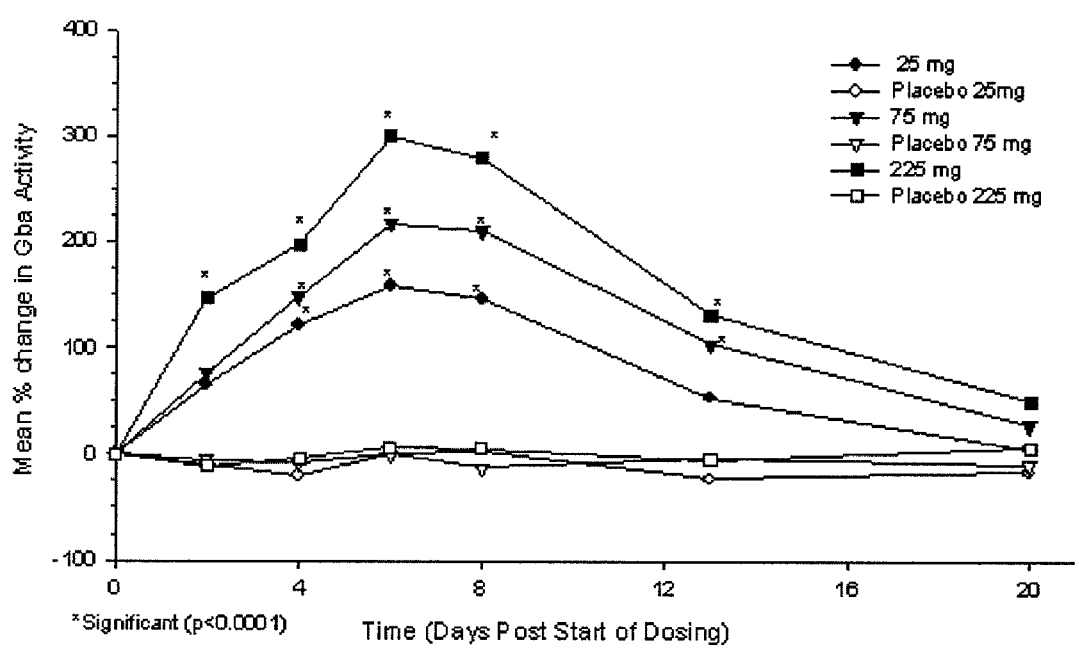
FIG. 1.

The present invention demonstrates a response to treatment with SPCs in a Gaucher disease model as evidenced by evaluation of specific surrogate markers of Gaucher disease following treatment. Accordingly, the present invention provides standards of care for evaluating response to SPC treatment in Gaucher patients by evaluating the patient for changes, i.e., improvements, in specific surrogate markers.

DEFINITIONS

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The term "Gaucher disease" includes Type 1, Type 2 and Type 3 (including 3a, 3b and 3c), and intermediates and subgroups thereof based on phenotypic manifestations.

A Gaucher disease patient refers to an individual who has been diagnosed with Gaucher disease due to a mutated acid β-glucosidase as defined further below.

A "mutated GCase" refers to a GCase protein that contains a mutation which affects folding and processing of the GCase protein in the ER. Accordingly, upon folding of the mutant into a proper conformation using a specific pharmacological chaperone, the mutated GCase protein will be able to progress or traffic from the ER through the Golgi to the lysosome. Mutations which impair folding, and hence, trafficking of GCase, can be determined by routine assays well known in the art, such as pulse-chase metabolic labeling with and without glycosidase treatment to determine whether the protein enters the Golgi apparatus, or fluorescent immunostaining for GCase localization within the cell. Specific embodiments of GCase folding mutants associated with neuronopathic diseases include but are not limited to: N370S, L444P, K198T, D409H, R496H, V394L, 84GG, and R329C.

"MIP" as used herein means macrophage inflammatory protein.

"TNF" means tumor necrosis factor.

"IL" means Interleukin.

"GM3" means ST3 beta-galactoside alpha-2,3-sialyltransferase 5, which is also known as, ST3GAL5 or ganglioside GM3.

As used herein, the term "specific pharmacological chaperone" ("SPC") refers to any molecule including a small molecule, protein, peptide, nucleic acid, carbohydrate, etc. that specifically binds to a protein and has one or more of the following effects: (i) enhancing the formation of a stable molecular conformation of the protein; (ii) inducing trafficking of the protein from the ER to another cellular location, preferably a native cellular location, i.e., preventing ER-associated degradation of the protein; (iii) preventing aggregation of misfolded proteins; and/or (iv) restoring or enhancing at least partial wild-type function and/or activity to the protein. A compound that specifically binds to e.g., GCase, means that it binds to and exerts a chaperone effect on GCase and not a generic group of related or unrelated enzymes. Following is a description of some specific pharmacological chaperones contemplated by this invention:

Isofagomine (IFG; (3R,4R,5R)-5-(hydroxymethyl)-3,4-piperidinediol) refers to a compound having the following structure:

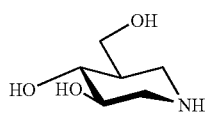

IFG has a molecular formula of $C_6H_{13}NO3$ and a molecular weight of 147.17. This compound is further described in U.S. Pat. Nos. 5,844,102 to Sierks et al., and 5,863,903, to Lundgren et al. N-alkyl IFG derivatives are described in U.S. Pat. No. 6,046,214.

C-benzyl-IFG, refers to a compound having the following structure:

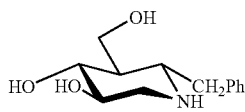

Other SPCs for GCase include hydroxypiperidine derivatives, which are described in pending PCT publications WO 2005/046611 and WO 2005/046612, and in U.S. patent application Ser. No. 10/988,428, filed Nov. 12, 2004. Also, chaperones for GCase include glucoimidazole and polyhydroxy-cyclohexenyl amine derivatives which are described in U.S. patent application Ser. No. 10/988,427 filed on Nov. 12, 2004.

As one example, glucoimidazole refers to a compound having the following structure:

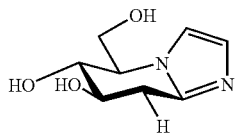

Still other SPCs for GCase are described in U.S. Pat. No. 6,599,919 to Fan et al., and include calystegine $A_3$, calystegine $A_5$, calystegine $B_1$, calystegine $B_2$, calystegine $B_3$, calystegine $B_4$, calystegine $C_1$, N-methyl-calystegine $B_2$, DMDP, DAB, castanospermine, 1-deoxynojirimycin, N-butyl-deoxynojirimycin, 1-deoxynojirimycin bisulfite, N-butyl-isofagomine, N-(3-cyclohexylpropyl)-isofagomine, N-(3-phenylpropyl)-isofagomine, and N-[(2E,6Z,10Z)-3,7,11-trimethyldodecatrienyl]-isofagomine.

A "surrogate marker" or "surrogate clinical marker" of Gaucher disease refers to the abnormal presence of, increased levels of, abnormal absence of, or decreased levels of a biomarker that is associated with Gaucher disease and that is a reliable indicator of Gaucher disease (but is not associated width a healthy individual) either alone or in combination with other abnormal markers or symptoms of Gaucher disease.

As non-limiting examples, surrogate markers of Gaucher disease, include decreased lysosomal GCase activity; the presence of lipid-laden macrophages ("Gaucher macrophages"); hepatosplenomagaly; increased chitotriosidase; increased pulmonary chemokine PARC/CCL18; increased levels of angiotensin converting enzyme (ACE) and total acid phosphatase; hematologic or immune abnormalities including anemia, thrombocytopenia, leukopenia, and hypergammaglobulinemia, T-lymphocyte deficiency in the spleen, systemic B cell hyperproliferation, plasmacytosis, the presence of inflammatory foci in tissue or organ comprising macrophages, lymphocytes, and neutrophils, elevated inflammatory cytokines (e.g., TNF-α, IL-1β, IL-6, IL-17, MIP-1α, VEGF), impaired neutrophil chemotaxis; imbalances in T cell and monocyte subsets; over-expression of cell membrane expression MHCII and Cd1d on monocytes; skeletal defects, including infiltration of Gaucher cells in the bone marrow, bone-specific alkaline phosphatase activity in plasma (BAP), lytic lesions, osteoschlerosis, bone pain, fractures, vertebral collapse, or reduced triglyceride presence; neurological symptoms such as neuronal loss, neurodegeneration, horizontal gaze abnormalities, myoclonic movements, corneal opacity, ataxia, dementia, and spasticity; and pulmonary infiltration of Gaucher macrophages, possibly leading to pulmonary hypertension, pulmonary and activation regulated chemokine (PARC) activity in plasma, and tartrate-resistant acid phosphatase 5b (TRACP 5b) activity in plasma.

Other surrogate markers are present at the sub-cellular level ("sub-cellular surrogate markers") and include aberrant trafficking of GCase in cells from Gaucher patients from the ER to the lysosome; aberrant trafficking of lipids though the endosomal pathway; the presence of increased amounts misfolded GCase in the ER or cytosol; the presence of ER and/or cell stress resulting from toxic accumulation of GCase (as determined by gene and/or protein expression of stress-related markers); aberrant endosomal pH levels; aberrant cell morphology; suppression of the ubiquitin/proteasome pathway; or an increase in the amount of ubiquitinated proteins.

An "an improvement in a surrogate marker" refers to an effect, following treatment with an SPC, of the amelioration or reduction of one or more clinical surrogate markers which are abnormally present or abnormally elevated in Gaucher disease, or the presence or increase of one or more clinical surrogate markers which are abnormally decreased or absent in Gaucher disease, relative to a healthy individual who does not have Gaucher disease, and who does not have an other disease that accounts for the abnormal presence, absence, or altered levels of that surrogate marker.

A "responder" is an individual diagnosed with a disease associated with a Gba mutation which causes misfolding of the GCase protein, such as Gaucher disease, and treated according to the presently claimed method who exhibits an improvement in, amelioration of, or prevention of, one or more clinical symptoms, or improvement in one or more surrogate markers referenced above.

In addition, a determination whether an individual is a responder can be made at the sub-cellular level by evaluating improvements in the sub-cellular surrogate markers, e.g., intracellular trafficking of the mutant GCase protein in response to treatment with an SPC. Restoration of trafficking from the ER is indicative of a response. Other sub-cellular evaluations that can be assessed to determine if an individual is a responder include improvements in the above-referenced sub-cellular surrogate markers.

The terms "therapeutically effective dose" and "effective amount" refer to the amount of the specific pharmacological chaperone that is sufficient to result in a therapeutic response. A therapeutic response may be any response that a user (e.g., a clinician) will recognize as an effective response to the therapy, including improvements in the foregoing symptoms and surrogate clinical markers. Thus, a therapeutic response will generally be an amelioration of one or more symptoms of a disease or disorder, such as those described above.

The phrase "pharmaceutically acceptable" refers to molecular entities and compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

Formulations, Dosage, and Administration

IFG and derivatives can be administered in a form suitable for any route of administration, including e.g., orally in the form tablets, capsules, or liquid, or in sterile aqueous solution for injection. In a specific embodiment, the IFG tartrate is administered as a powder-filled capsule. IFG tartrate is described in pending provisional patent applications 60/808,020 and 60/890,719, herein incorporated by reference. When the compound is formulated for oral administration, the tablets or capsules can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art.

Liquid preparations for oral administration may take the form of, for example, solutions, syrups or suspensions, or they may be presented as a dry product for constitution with water or another suitable vehicle before use. Such liquid preparations may be prepared by conventional means with pharmaceutically acceptable additives such as suspending agents (e.g., water, sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled or sustained release of the ceramide-specific glucosyltransferase inhibitor.

The pharmaceutical formulations of IFG or derivatives suitable for parenteral/injectable use generally include sterile aqueous solutions, or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be brought about by various antibacterial and antifungal agents, for example, parabens, chlorobutanol, phenol, benzyl alcohol, sorbic acid, and the like. In many cases, it will be reasonable to include isotonic agents, for example, sugars or sodium chloride. Prolonged absorption of the injectable compositions can be brought about by the use in the compositions of agents delaying absorption, for example, aluminum monosterate and gelatin.

Sterile injectable solutions are prepared by incorporating IFG or derivatives in the required amount in the appropriate solvent with various of the other ingredients enumerated above, as required, followed by filter or terminal sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The above formulations can contain an excipient or excipients. Pharmaceutically acceptable excipients which may be included in the formulation are buffers such as citrate buffer, phosphate buffer, acetate buffer, and bicarbonate buffer, amino acids, urea, alcohols, ascorbic acid, phospholipids, proteins, such as serum albumin, collagen, and gelatin; salts such as EDTA or EGTA, and sodium chloride; liposomes; polyvinylpyrollidone; sugars such as dextran, mannitol, sorbitol, and glycerol; propylene glycol and polyethylene glycol (e.g., PEG-4000, PEG-6000); glycerol, glycine or other amino acids and lipids. Buffer systems for use with the formulations include citrate, acetate, bicarbonate, and phosphate buffers. Phosphate buffer is a preferred embodiment.

The formulations can also contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

Administration

The route of administration of IFG or derivatives may be oral (preferably) or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations of IFG or derivatives may be by periodic injections of a bolus of the preparation, or may be administered by intravenous or intraperitoneal administration from a reservoir which is external (e.g., an i.v. bag) or internal (e.g., a bioerodable implant). See, e.g., U.S. Pat. Nos. 4,407,957 and 5,798,113, each incorporated herein by reference. Intrapulmonary delivery methods and apparatus are described, for example, in U.S. Pat. Nos. 5,654,007, 5,780,014, and 5,814,607, each incorporated herein by reference. Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Needle-less injector devices are described in U.S. Pat. Nos. 5,879,327; 5,520,639; 5,846,233 and 5,704,911, the specifications of which are herein incorporated by reference. Any of the formulations described above can be administered using these methods.

Furthermore, a variety of devices designed for patient convenience, such as refillable injection pens and needle-less injection devices, may be used with the formulations of the present invention as discussed herein.

Dosage

Persons skilled in the art will understand that an effective amount of the IFG or derivatives used in the methods of the invention can be determined by routine experimentation, but is expected to be an amount resulting in serum levels between 0.01 and 100 μM, preferably between 0.01 and 10 μM, most preferably between 0.05 and 1 μM. The effective dose of the compounds is expected to be between 0.5 and 1000 mg/kg body weight per day, preferably between 0.5 and 100, most preferably between 1 and 50 mg/kg body weight per day. In a specific embodiment, the dose is between about 10-600 mg/day, more specifically 25-300 mg/day, more specifically, 50-150 mg/day, or at appropriate intervals as determined. For example, two dosing regimens contemplated include treatment with 150 mg/day IFG tartrate for about 7 days, followed by interval dosing of about every 4 or every 7 days thereafter.

Gaucher Disease Treatment Monitoring Using Surrogate Markers

The present invention provides a method for monitoring the treatment of Gaucher patients with specific pharmacological chaperones. Specifically, various assays are employed to evaluate the progress of the disease and its response to treatment with IFG. In particular, various systemic and subcellular markers can be assayed. The monitoring aspect of the present invention encompasses both invasive and non-invasive measurement of various cellular substances.

Glucosylceramide (GluCer) accumulation. GluCer is glycolipid that pathologically accumulates in Gaucher patients, primarily in Type 1 and Type III patients. Levels can be measured in urine and in plasma and tissues using a variety of accepted methods. In addition, one prevalent Gaucher surrogate marker is the presence of the "Gaucher macrophage." The Gaucher macrophage is an enlarged, lipid-laden macrophage that has a distinct morphology indicative of an activated macrophage.

Notably accumulation GluCer only presents only in the macrophages of individuals with Type I Gaucher disease. The presence of Gaucher macrophages is easily assessed morphologically by e.g., hematoxylin and eosin staining and microscopy.

Acid β-glucosidase activity. Decreased GCase is associated with all three types of Gaucher disease. As indicated above, non-invasive assessment of GCase activity can be evaluated of peripherally lymphocytes and polymorphonuclear cells (PMNs) derived from Gaucher patients. Cultured fibroblasts from skin biopsies can also be used. Such assays typically involve extraction of blood leukocytes from the patient, lysing the cells, and determining the activity upon addition of a substrate such as 4-methyl umbelliferyl beta-D-glucoside, or 4-heptyl-umbelliferyl-beta-D-glucoside (see e.g., Forsyth et al., *Clin Chim Acta.* 1993; 216(1-2):11-21; Beautler et al., *J Lab Clin Med.* 1970; 76:747-755. Another assay employs the use of short-acyl chain substrate, N-(1-hexanoyl)-D-erythro-glucosylsphingosine (hexanoyl-GlcCer). A strict correlation was observed between levels of hexanoyl-GlcCer hydrolysis and Gaucher type in human skin fibroblasts (Meivar-Levy et al., *Biochem J.* 1994; 303 (Pt 2):377-82).

Flow cytometry can also be used to evaluate GCase activity in patient cells (Lorincz et al., *Blood.* 1997; 189: 3412-20; and Chan et al., *Anal Biochem.* 2004; 334(2):227-33). This method employed the fluorogenic GCase substrate CMFD-Glu which was loaded into cells by pinocytosis. The cells were then evaluated using conventional fluorescein emission optics. Levels of fluorescence correlate with the amount of GCase activity.

Cell morphology. Ultrastructural analysis of blood leukocytes and PMNs has been described (Laslo et al., *Acta Paediatr. Hung.* 1987; 28: 163-73). Briefly, electron microscopy revealed pathology in vacuole formations in patients with Gaucher disease. This method can also be used to determine the presence of Gaucher macrophages.

Chitotriosidase. Type 1 Gaucher patients have elevated activity of the enzyme chitotriosidase (chitinase 1) in plasma (Hollak et al., *J. Clin. Invest.* 1994; 93: 1288-92). Chitotriosidase is a 39 kDa human chitin hydrolase (chitinase). The function of this enzyme in Gaucher disease in unclear since its substrate, chitin, a component found in bacterial cell walls, fungi, nematodes and other pathogens. In the plasma of almost all symptomatic Gaucher patients, but not pre-symptomatic individuals, chitotriosidase (chitinase) activity is at least 100-fold (and up to 600-fold) increased above normal values. In asymptomatic individuals, chitotriosidase activity is also elevated, and is intermediate between normal individuals and symptomatic Gaucher patients. The chitotriosidase is secreted by the Gaucher macrophages and PMNs, and is reduced upon supplementation with wild-type GCase in ERT.

It has been suggested that chitotriosidase activity above 15,000 nmol ml$^{-1}$ h$^{-1}$ indicates necessity for treatment for Gaucher disease (Aerts et al., *Phil. Trans. R. Soc. Lond.* B 2003; 358: 905-14). Numerous assays can be used to detected elevated chitotriosidase, including but not limited to detection of enzyme activity in cells isolated from patients by addition of a substrate for the enzyme. One such substrate is substrate molecule, 4-methylumbelliferyl-(4-deoxy)chitobiose. An assay employing this substrate for chitotriosidase activity is described in Aguilara et al., *J Biol Chem.* 2003; 278(42): 40911-6.

Hyperlipidemia. Gaucher patients show decreased plasma total cholesterol, low-density lipoprotein cholesterol (LDL) and high-density lipoprotein cholesterol (HDL) levels, as well as decreased apolipoprotein (apo) A-I and B. Conversely, concentrations of plasma apo E are elevated. Analysis of cholesterol levels can be achieved by routine cholesterol testing.

Bone marrow analysis. As indicated above, Gaucher patients exhibit infiltration of Gaucher cells in the bone marrow. In addition to bone marrow biopsies (aspiration) to detect the Gaucher macrophages, magnetic resonance (MR) imaging of bone marrow has recently been described (Poll et al., *Skleletal Radiol.* 2001; 30: 496-502). This study evaluated Gaucher patients following ERT and used MR to evaluate changes in the appearance of yellow marrow. Increased signal intensity demonstrated partial reconversion of fatty marrow following treatment, in contrast with non-homogenous, patchy signal intensity in patients with Gaucher having bone infarcts.

In addition, quantitative chemical shift imaging has been applied to study the triglyceride content of lumbar bone marrow (Hollak and Aerts, *J. Inherit. Metab. Dis.* 2001; 24: 97-105). Triglyceride content is lower due to displacement of triglyceride adipocytes by the Gaucher macrophages. Thus, a correction in bone marrow fat content following therapy is predictive for the occurrence of bone complications.

Bone analysis. Skeletal manifestations of Gaucher disease range from asymptomatic Erlenmeyer flask deformity of the distal femora to pathologic fractures, vertebral collapse, lytic lesions, and acute bone crises which result from episodes of bone infarction, leading to osteoschlerosis. Osteopenia, osteonecrosis, avascular necrosis also present. Bone pain is associated with skeletal involvement. Skeletal manifestations of Gaucher disease can be detected and evaluated using skeletal radiography, and dual-energy x-ray absorptiometry (DEXA) scanning has been used to assess osteopenia.

In one embodiment, DKK1 levels are measured, in which lower levels of DKK1 is indicative of Gaucher Disease.

Biochemical indices of bone involvement can be measured using markers of bone metabolism and lumbar BMD such as serum concentrations of calcium, phosphorus, bone-specific alkaline phosphatase, carboxyterminal propeptide of type I procollagen (PICP), carboxyterminal telopeptide of type I collagen (ICTP), osteocalcin, intact parathyroid hormone), and urinary calcium, phosphorus, hydroxyproline and free deoxypyridinoline (Clana et al., *J Inherit Metab Dis.* 2005; 28(5):723-32).

Hematologic manifestations. Hematologic manifestations of Gaucher disease include cytopenia and acquired coagulopathy caused by deficiency of factor XI. When cytopenia occurs following splenectomy, there presents marrow infiltration by Gaucher cells. Thrombocytopenia, anemia and leucopenia are especially prevalent. Impaired immunologic abnormalities in Gaucher disease, include hypergammaglobulinemia, T-lymphocyte deficiency in the spleen, and impaired neutrophil chemotaxis. Other immune abnormalities include systemic B cell hyperproliferation, plasmacytosis, the presence of inflammatory foci in tissue or organ comprising macrophages, lymphocytes, and neutrophils, and elevated inflammatory cytokines (e.g., TNF-$\alpha$, IL-1$\beta$, IL-6, IL-8, IL-17, MIP-1$\alpha$ and VEGF). Evaluation of the foregoing can be achieved using routine biochemical tests, such as CBC to determine cytopenia.

In one embodiment, where patients with Gaucher disease have been or are currently being treated with Enzyme Replacement Therapy (ERT) and/or Substrate Reduction Therapy (SRT) IL-1$\alpha$, IL-1$\beta$, IL-6 and IL-7 are excluded as surrogate markers for Gaucher Disease whereas for ERT and/or SRT naïve patients or patients that have been off ERT and/or SRT long enough for IL-1$\alpha$, IL-1$\beta$, IL-6 and IL-7 levels to return to pre-ERT and/or pre-SRT levels, IL-1$\alpha$, IL-1$\beta$, IL-6 and IL-7 are included as surrogate markers for Gaucher Disease.

In addition, increased cell membrane expression of MHCII antigens and the lipid-binding molecule CD1d have been observed on monocytes from Type 1 Gaucher patients, suggesting an impairment in endosomal trafficking of lipids (Balreira et al., *Br. J. Haematology.* 2005; 129: 667-76). Treatment with ERT alleviated the MHCII overexpression, and restored the balance of T cell subsets in those patients. As such, MHCII and CD1d are biomarkers of Gaucher disease, whose overexpression can be monitored on monocytes from patients treated with chaperone therapy using, e.g., FACS analysis and/or reverse transcriptase PCR.

Pulmonary biomarkers. Type 1 Gaucher patients often exhibit pulmonary hypertension, especially following splenectomy. This correlates with increased severity of the disease. Diagnosis of PH can be achieved by assessing ventricular systolic pressure (RVSP) using Doppler echocardiography. Echocardiography is routinely performed to assess tricuspid incompetence (TI) gradient, as an indirect measure of pulmonary artery pressure. Other markers of pulmonary function abnormalities include airways obstruction, reduced expiratory flows, reduction in lung volumes, and alveolar-capillary diffusion abnormality. These parameters can be assessed by observing e.g., reduced functional residual capacity, and reduction of total lung capacity and signs of airtrapping. Functional residual capacity (FRC) can be measured by the classic open-circuit, nitrogen wash-out technique and standard spirometry. Airtrapping is evidence by elevated residual volume or residual volume/total lung capacity). Chest x-rays also can be used to assess the extent of pulmonary manifestations. Lastly, high-resolution CT (HRCT) can be used to assess for adverse changes in the vertebrae which can also contribute to pulmonary abnormalities.

In Gaucher disease, a pulmonary chemokine designated PARC/CCL18, has been identified as a biomarker for clinical development that reflects disease severity and response to treatment (Cox et al., *Acta Paediatr Suppl.* 2005; 94(447):39-42). Elevated levels of PARC/CCL18 (10-50-fold) in Gaucher patients, were shown to be a reliable indicator of increased splenic and liver volume, and decreased platelet count.

Organomegaly. Physical examination in all Types of Gaucher disease usually reveals the presence of hepatosplenomegaly. Splenomegaly can have a range from a 5-fold to more than 80-fold increase in size when adjusted for body weight Nodules on the surface of the spleen may represent regions of extramedullary hematopoiesis, collections of Gaucher cells, or resolving infarcts. Subcapsular splenic infarcts=can present as localized abdominal pain. Short stature and wasting occasionally are found in patients with massive organomegaly.

Hepatomegaly occurs in more than 50% of patients with type 1 Gaucher disease, and in most patients with Types 2 and 3 disease. Liver volumes range from normal to about 8.7-fold over normal. Hepatic glucocerebroside levels are elevated from 25 fold to 400-fold. Minor elevations of liver enzymes such as AST and ALT are common, even in patients who are affected mildly with Gaucher disease, but the presence of jaundice or impaired hepatocellular synthetic function is a poor prognostic indicator. On liver biopsy, glycolipid-laden Gaucher cells are evident in the sinusoids.

Ultrasonography of the abdomen or MR imaging can determine extent of organomegaly in Gaucher patients.

Neurological and ocular symptoms. Types 2 and 3 Gaucher disease are associated with neuronopathic symptoms due to accumulation of GluCer and its metabolite in the brains of patients. Such symptoms include neuronal loss, neurodegeneration, horizontal gaze abnormalities, myoclonic movements, corneal opacity, ataxia, dementia, spasticity, auditory abnormalities, abnormal EEG/seizures, cognitive impairment, and progressive bulbar palsy. Particular eye movement abnormalities include horizontal Saccade Initiation Failure (hSIF) (also known as ocular motor apraxia), Horizontal Saccade Slowing, Vertical Saccade Initiation Failure (vSIF) (especially downward), Vertical Saccade slowing (especially downward), and 6th nerve paresis.

In addition, accumulation of lipid in vitreous bodies from Gaucher disease patients with vitreous opacities was detected with the extraction matrix-assisted laser desorption ionization time-of-flight mass spectrometry (DE MALDI-TOF-MS) method (Fujiwaki et al., *J Chromatogr B Analyt Technol Biomed Life Sci.* 2004; 806(1):47-51).

Cardiovascular. A type 3 Gaucher phenotype with calcification of the aortic and mitral valves has also been identified (George et al., *Clin Genet.* 2001; 59(5):360-3).

Other surrogate markers. Angiotensin converting enzyme (ACE) and as is total acid phosphatase also are elevated in Gaucher patients.

It is to be understood that these markers can be used to monitor treatment only if they are identified to be abnormal prior to treatment. For example, about 5-6% of the population is unable to express chitotriosidase due to a gene mutation. It is axiomatic that chitotriosidase would not be elevated in Gaucher patients having this gene defect. As such, chitotriosidase would not be an appropriate surrogate marker with which to assess treatment. In addition, it is preferable that the abnormal elevation of the markers be correlated with the presence of the disease, and not attributed to other causes or concomitant diseases such as liver disease, avascular necrosis, osteoporosis, or gammopathy.

Molecular Biology Monitoring Assays to Detect Sub-Cellular Markers

Monitoring of treatment of Gaucher disease with specific pharmacological chaperones can be done at the sub-cellular level in addition to the systemic or macroscopic level, described above. For example, disturbances in endosomal-lysosomal membrane trafficking of lipids to the Golgi complex are characteristic of lysosomal storage disease (Sillence et al., *J Lipid Res*. 2002; 43(11):1837-45). Accordingly, one way of monitoring treatment of Gaucher would be to contact cells from patients with labeled lipid (BODIPY-LacCer) and monitor its trafficking in endosomal structures. Pathological accumulation in endosomal structures, for example, would be indicative that the patient is not responding well to treatment.

As one example, pH-sensitive fluorescent probes that are endocytosed by the cells can be used to measure pH ranges in the lysosomes and endosomes (i.e. fluorescein is red at pH 5, blue to green at 5.5 to 6.5). Lysosome morphology and pH will be compared in wild type and chaperone treated and untreated patient cells. This assay can be run in parallel with the plate reader assay to determine the pH-sensitivity. For example, BODIPY-LacCer is trafficked to the Golgi in normal cells, but accumulates in the lysosomes of cells with lipid storage disorders. BODIPY-LacCer fluoresces green or red depending on the concentration in the membrane, and the green/red color ratio in the lysosome can be used to measure changes in concentration. Living healthy cells and patient cells, treated and untreated with compounds, will be incubated with BODIPY-LacCer and the red/green color ratio can be measured by the FACS and/or confocal microscope and the staining pattern (lysosome vs. Golgi) can be determined using a confocal microscope.

Trafficking occurs in cells along pH gradients (i.e. ER pH about 7, Golgi pH about 6.2-7.0, trans-Golgi network pH about 6.0, early and late endosomes pH about 6.5, lysosomes pH about 4.5) and luminal and endosomal pH is disrupted in cells with trafficking defects such as Gaucher cells. Accordingly, an assay to determine pH sensitivity in wild type, SPC-treated and untreated patient cells, if correlated to positive effects of pH on trafficking, can be used to monitor restoration of trafficking in Gaucher patients. If patient cells are more sensitive to changes in pH, than it would be possible to create a screening assay for SPCs that reduce the cells pH sensitivity, restores lysosome morphology or function, or more generally restores normal trafficking.

In addition, mitigation of the trafficking defect can be assessed at the molecular level by determining co-localization of the deficient enzyme (GCase) with a lysosomal marker such as Lyso-Tracker®. Localization of GCase in the lysosome is evidence that trafficking from the ER to the lysosome is restored by treatment with the specific pharmacological chaperone. Such an assay is described below in Example 3. In brief, normal and patient cells, treated and untreated with SPCs, are fixed and stained with primary antibodies to the enzyme and endosome/lysosome markers (e.g., Rab7, Rab9, LAMP-1, LAMP-2, dystrophin-associated protein PAD) and fluorescently tagged secondary antibodies. The FACS and/or confocal microscope is used to quantify the amount of fluorescence due to the concentration of enzyme and other endocytic pathway markers, and the confocal microscope can be used to determine changes in staining patterns.

In addition, traditional biochemical methods, such as pulse-chase metabolic labeling combined with Endoglycosidase H treatment. Endo H only cleaves proteins which have acquired ER glycosylation (high mannose N-linked), i.e., which are localized ER, but will not cleave proteins that have made it out of the ER to the Golgi and have acquired additional glycosylation in the Golgi. Accordingly, the greater the level of Endo H sensitive GCase, the more accumulation of the protein in the ER. If the GCase has made it into the Golgi, the glycosidase PNGase F can be used to confirm whether the protein has exited the Golgi since it cleaves all N-linked sugars.

ER Stress. The toxic accumulation of misfolded proteins in the ER of cells, such as the misfolded GCase in Gaucher patients, often results in ER stress. This leads to induction of the cell stress response which attempts to resolve the disruption in cell homeostasis. Accordingly, measuring markers of ER stress in patients following treatment with the specific pharmacological chaperone provides another way to monitor the effects of treatment. Such markers include genes and proteins associated with the Unfolded Protein Response, which include BiP, IRE1, PERK/ATF4, ATF6, XBP1 (X-box binding factor 1) and JNK (c-Jun N-terminal kinase). One method to assess ER stress is to compare expression levels between wild type and Gaucher patient cells, and also between SPC-treated and untreated cells. ER stress inducers (e.g., tunicamycin for the inhibition of N-glycosylation and accumulation of unfolded proteins in the ER, lacatcystin or $H_2O_2$) and stress relievers (e.g., cyclohexamide to inhibit protein synthesis) can be used as controls.

Another method contemplated for monitoring the ER stress response is via gene chip analysis. For example, a gene chip with a variety of stress genes can be used to measure expression levels and type of ER stress response (early, late, apoptosis etc.). As one example, the HG-U95A array can be used. (Affymetrix, Inc.).

Lastly, since prolonged ER stress can result in apoptosis and cell death, depending on the level of unfolded proteins in the ER, and the resulting stress level, cells will be more or less sensitive to ER stress inducers such as tunicamycin or proteasome inhibitors. The more sensitive the cells are to the stress inducers, the higher the number of apoptotic or dead cells is observed. Apoptosis can be measured using fluorescent substrates analogs for caspase 3 (an early indicator of apoptosis). FACS, confocal microscopy, and/or using a fluorescence plate reader (96 well format for high through put assays) to determine the percentage of cells positive for apoptosis or cell death (FACS and/or confocal microscopy), or fluorescence intensity can be measured relative to protein concentration in a 96 well format with a fluorescence plate reader.

Another response to ER stress resulting from toxic protein accumulation in the ER is suppression of the ubiquitin/proteasome pathway. This leads to a general disruption of the endocytic pathway (Rocca et al., *Molecular Biology of the Cell*. 2001; 12: 1293-1301). Misfolded protein accumulation is sometimes correlated with increased amounts of polyubiquitin (Lowe et al., *Neuropathol Appl Neurobiol.* 1990; 16: 281-91).

Proteasome function and ubiquitination can be assessed using routine assays. For example, evaluation of 26S proteasome function in living animals by imaging has been achieved ubiquitin-luciferase reporter for bioluminescence imaging (Luker et al., *Nature Medicine.* 2003. 9, 969-973). Kits for proteasome isolation are commercially available from, for example, Calbiochem (Cat. No. 539176). Ubiquitination can be examined by morphological studies using immunohistochemistry or immunofluorescence. For example, healthy cells and patient cells, treated and untreated with SPCs, can be fixed and stained with primary antibodies to ubiquitinated proteins and fluorescence detection of secondary antibodies by FACS and/or confocal microscopy will be used to determine changes in ubiquitinated protein levels.

Another assay to detect ubiquitinated proteins is AlphaScreen™ (Perkin-Elmer). In this model, the GST moiety of a GST-UbCH5a fusion protein is ubiquitinated using biotin-Ubiquitin (bio-Ub). Following ubiquitin activation by E1, in the presence of ATP, bio-Ub is transferred to UbCH5a. In this reaction, UbCH5a acts as the carrier to transfer the bio-Ub to its tagged GST moiety. The protein which becomes biotinylated and ubiquitinated is then captured by anti-GST Acceptor and streptavidin. Donor beads resulting in signal generation. No signal will be generated in the absence of ubiquitination.

Lastly, an ELISA sandwich assay can be used to capture ubiquitinated mutant GCase. The primary antibody to the GCase (e.g., rabbit) would be absorbed to the surface, enzyme would be captured during an incubation with cell lysate or serum, then an antibody (e.g., mouse or rat) to ubiquitinated protein, with secondary enzyme-linked detection, would be used to detect and quantify the amount of ubiquitinated enzyme. Alternatively, the assay could be used to quantify the total amount of multi-ubiquitinated proteins in cell extract or serum.

Combination Therapy

The therapeutic monitoring of the present invention is also applicable following treatment of patients with a combination of IFG and derivatives and ERT or gene therapy. Such combination therapy is described in commonly-owned, U.S. patent application publication number 2004/0180419 (Ser. No. 10/771,236), and in U.S. patent publication 2004/0219132 (Ser. No. 10/781,356). Both applications are herein incorporated by reference in their entirety.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification. The invention is therefore to be limited only by the terms of the appended claims along with the full scope of equivalents to which the claims are entitled.

Example 1

Phase I Studies of the Safety, Pharmacokinetics and Pharmacodynamics of IFG Tartrate for the Treatment of Gaucher Disease Using cell-based and animal models it has been shown that isofagomine increases cellular levels of glucocerebrosidase (GCase), the enzyme deficient in Gaucher disease. Randomized double-blind Phase I clinical studies were performed in 72 healthy volunteers, (39 male, 33 female). Isofagomine tartrate was orally administered as an aqueous solution. In a first-in-human single ascending dose study, doses of 8, 25, 75, 150 (two cohorts), and 300 mg were administered (6 active, 2 placebo in each cohort). In a multiple ascending dose study, doses of 25, 75, and 225 mg were administered daily for seven days (6 active, 2 placebo in each cohort). In both studies, isofagomine tartrate was generally well tolerated at all doses and treatment-emergent adverse events in both studies were mostly mild. No serious adverse events occurred.

Isofagomine tartrate showed good systemic exposure via the oral route. In the single-dose study, plasma AUC and Cmax values were linearly correlated with administered dose. Mean plasma levels peaked at 3.4 hr. (SEM: 0.6 hr.) and the plasma elimination half-life was 14 hr. (SEM: 2 hr.). In the multiple-dose study, after 7 days of oral administration, the pharmacokinetic behavior was found to be linear with dose, with no unexpected accumulation of isofagomine tartrate. Tmax and half-life values were similar to those observed in the single-dose study.

In the multiple-dose study, GCase activity in isolated white blood cells was measured at days 1, 3, 5 and 7 during administration of isofagomine tartrate, and at days 9, 14 and 21 during the post-treatment washout period. In all subjects receiving isofagomine tartrate there was a marked increase in GCase levels during the drug treatment period, followed by a decrease upon removal of the drug and a return to near baseline levels by day 21 (FIG. 1). The increase in enzyme level was dose-related, reaching approximately 3.5-fold above baseline levels. These results for the safety, pharmacokinetics and preliminary pharmacodynamic effects in healthy volunteers support the further evaluation of isofagomine tartrate for the treatment of Gaucher disease.

Example 2

Determination of Surrogate Markers of Gaucher Disease in L444P Transgenic Mice Treated with Specific Pharmacological Chaperones L444P transgenic mice (homozygous for human L444P mutated Gba on a glucosylceramide synthase null background) exhibit multi-system inflammation; B cell hyperproliferation; deficiency in GCase activity in the brain, liver, spleen, and lung; increased liver and spleen weights; elevated plasma levels of chitotriosidase at 3 months; and elevated plasma levels of IgG (Mizukami et al., *J. Clin. Inves.* 2002; 109: 1215-21). However, due to the disruption in the glucosylceramide synthase gene, these mice do not exhibit accumulation of GluCer in e.g., macrophages. Concomitant glucosylceramide synthase disruption is necessary since previously made L444P transgenic mice died within 3 days of birth due to impaired permeability barrier function in the epidermis.

In this experiment, the L444P transgenic mice were treated with isofagomine or C-benzyl-isofagomine and surrogate markers were measured at 1, 3, 6 and 12 months to determine efficacy of the chaperones. In addition, mice in a "washout" period of 2 weeks of non-chaperone treatment following 4 weeks of treatment were also evaluated for reversion of surrogate markers back to levels seen in untreated controls.

Methods

Isofagomine treatment. Mice were administered isofagomine tartrate in their drinking water, ad libitum, at a concentration of 20 mg/kg.

Surrogate marker measurement. At the end of 4, 12, or 24 weeks, mice were sacrificed and evaluated for (i) enhancement of GCase enzyme activity in liver, spleen, lung and brain; (ii) chitotriosidase activity; (ii) body, spleen, and liver weight; and (iv) serum IgG, cholesterol, and liver enzyme levels. In addition, chaperone concentration in plasma and in the foregoing tissues will also be determined.

a. GCase activity assays in tissue: Liver, brain, spleen, and lung tissue is freshly harvested (blood washed away with PBS), or thawed from frozen stock. Tissue is minced tissue and homogenized on ice in 200-500 µl McIlvaine (MI) buffer (0.25% sodium taurocholate, 0.1% Triton x-100 in 0.1M citrate and 0.2M phosphate buffer, pH 5.2), and centrifuged at 10,000×g. The supernatant is collected and may be frozen at this step.

About 1-10 µl of supernatant from the tissue homogenates is added to a clear 96-well plate for the Micro BCA Protein Assay (Pierce, cat # 23235) to quantitate the amount of total protein according to the manufacturer's protocol. As a negative control, another 10 µl is added to a black plate, mixed with 10 µl of 2.5 mM CBE (2.7 mg Conduritol B Epoxide in 6.7 ml buffer), an inhibitor of GCase activity, and left at room temperature (RT) for 30 minutes. 50 µl of 3 mM 4-methal Umbelliferyl beta-D-glucoside (4-MU-beta-D-glucoside; made fresh, powder is dissolved in 0.2 ml of DMSO, then q.s. to proper volume with MI buffer), a GCase substrate, is then added, and the black plate is further incubated at 37° C. for 1 hr. After incubation, 10 µl of supernatant is added to a second black plate, mixed with 10 µl of MI buffer and 50 µl 6 mM of GCase substrate 4-MU-beta-D-glucoside, and incubated at 37° C. for 1 hr. The reaction is then stopped by adding 70 µl 0.2 M glycine, pH 10.8. The plate is read in a plate-reader (Victor2 1420 multilabel counter; Wallac) at $F_{460}$.

Relative beta-glucose activity is determined by the following equation:

$$F_{460} \text{ without CBE} - F_{460} \text{ with CBE}/(A_{550} \text{ sample} - A_{550} \text{ buffer})$$

$F_{460}$ reading is converted into nmole 4-MU based on 4-MU standard curve and $A_{550}$ is converted into mg of protein based on the protein standard curve. One unit of GCase activity is defined as nmole of 4-MU released in one hour.

b. Body and tissue weight measurements: Animals were weighed prior to sacrifice after 4, 3, 6 and 12 months. Following sacrifice, spleen and liver were removed and weighed.

c. Chitotriosidase activity: Plasma is collected for the assay in 5 µl aliquots (in duplicate), and the remaining is stored at −80° C. 5 µl of plasma/EDTA is mixed with 100 µl 22 µM 4-MU-b-D-N,N'N"-triacetylchitotriose in citrate phosphate buffer (0.1M citrate and 0.2M phosphate buffer, pH5.2; made by mixing 185 ml 0.1 M citric acid and 200 ml 0.2 M sodium phosphate) in a 96 well black plate. 5 µl of EDTA/PBS (no plasma) is used as a negative control. A standard curve with standard serum is prepared by serial dilution in one row of the plate. The plate is then incubated for 15 minutes at 37° C. (floating in a hot water bath), and the reaction stopped by adding 150 µl 1M glycine, pH 10.8. The plate is read at $F_{355}/F_{460}$ in a Victor$^2$ 1420 multilabel counter (Wallac).

d. IgG measurement: The mouse IgG ELISA quantitation kit (Bethyl Laboratories, Cat # E90-131) was used for determination of IgG concentration in plasma. 96-well plates were coated with 100 µl of the coating buffer (made by dissolving 1 capsule of coating antigen in 100 ml of double deionized water) and incubated for 1 hr at room temperature. The wells were then washed 3 times with 150 µl of wash buffer (50 mM Tris HCl (pH 8.0); 0.14 M NaCl; 0.05% Tween 20) followed by aspiration after each wash). Following washing, 200 µl of blocking solution was added (50 mM Tris HCl (pH 8.0); 0.14 M NaCl; 1% BSA), and the plates were incubated either at RT for 1 hour or at 4° C. overnight. Following incubation, the wells were washed 3× again with wash buffer, and 95 µl of sample diluent buffer (50 mM Tris HCl, pH 8.0; 0.14 M NaCl; 0.05% Tween 20; 1% BSA) and 5 µl of test plasma were added to the wells and incubated for an hour at RT.

As a standard, 100 µl of the serial diluted standard mouse IgG antibody of known concentration was added to one row of wells (diluted in diluent buffer at concentrations of 5000 ng/ml to 7.8 ng/ml).

Following incubation, wells were washed 5 times with wash buffer to remove the unbound sample 100 µl of secondary antibody (1:20000 in diluent buffer) was added, followed by incubation again for 1 hour at RT. Following washing (5×) to remove the unbound sample, 100 µl of developer (equal proportions of reagent A and B) were added to each well and incubated for 20 minutes at RT. The reaction was stopped by adding 100 µl of 1M phosphoric acid, and the color intensity was measured at 450 nm in the plate reader.

e. Cholesterol and liver enzyme measurement. These were measured according to ordinary techniques.

Washout study. To determine if and in what time frame the effects of drinking water dosed isofagomine on L444P mice regress after cessation of the treatment, a washout study was performed. Nine male 3 month old L444P mice were dosed at about 10 mg/kg/day for 4 weeks with an equal number of mice untreated as a control. Four treated and four untreated mice were sacrificed at the end of 4 weeks, and the remaining animals were not further treated with isofagomine, i.e., they were given normal drinking water, for another two weeks prior to sacrifice and evaluation of the above-described surrogate markers.

Results

Figure 2:
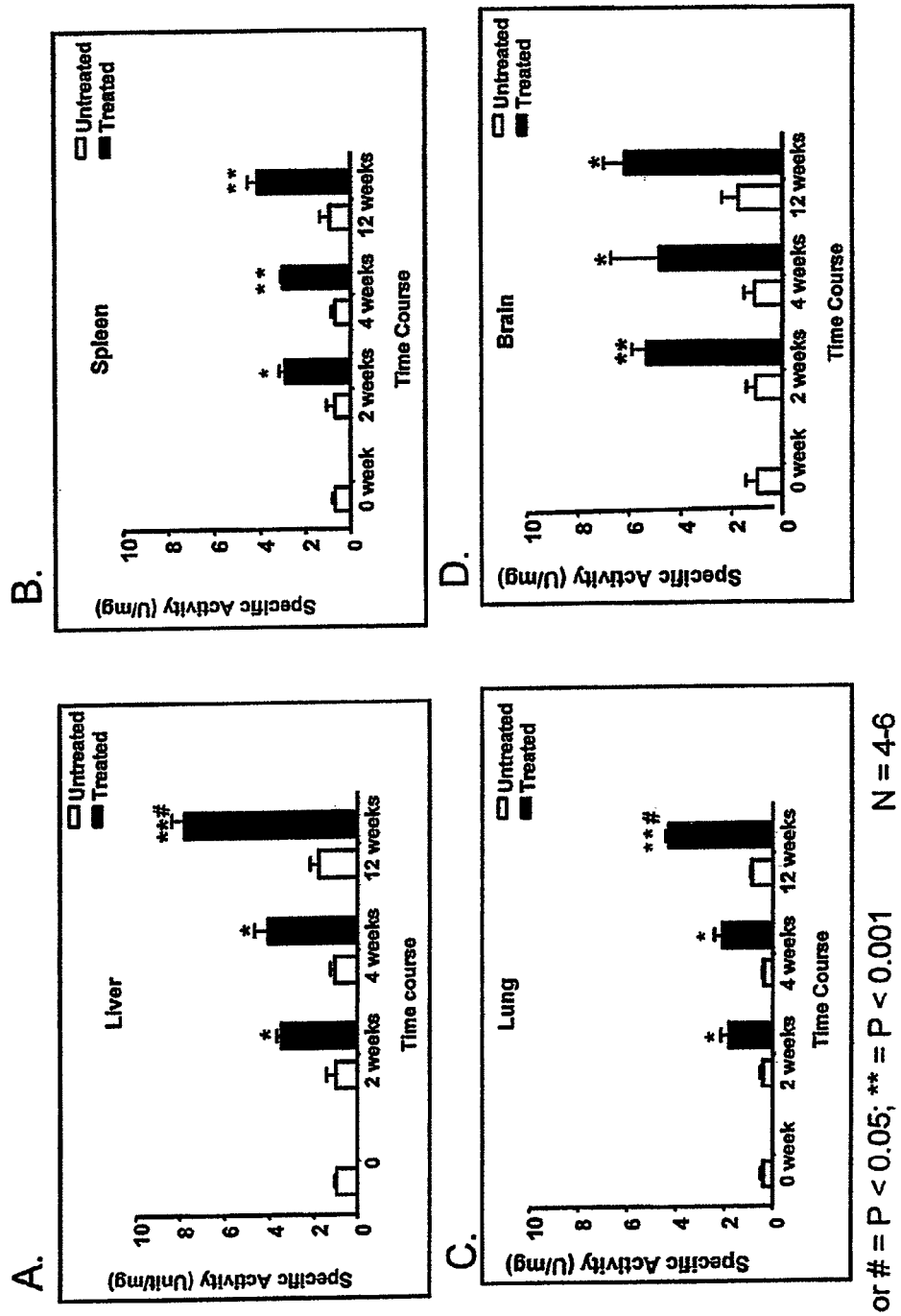
FIG. 2 depicts changes in GCase activity in liver (2A), spleen (2B), lung (2C), and brain (2D), following treatment with isofagomine (IFG).

GCase Activity in Tissue. Significant increase in GCase activity was observed after as little as two weeks of treatment with isofagomine in liver, spleen lung and brain (FIG. 2A-D), which persisted through 4-12 weeks. Notably, in brain, isofagomine treatment resulted in an increase from about 1 U/mg in untreated mice, to about 4.5 U/mg after 2 and 4 weeks of treatment, and further increased to about 6 U/mg after 12 weeks (p<0.001) (FIG. 2B). It is expected that increased GCase activity will persist at 3, 6 and 12 months and for as long as the chaperones are administered.

Similarly, after two weeks, the C-benzyl-isofagomine-treated mice also exhibited significant increased GCase activity in the spleen, and a trend toward increased activity in the lung and brain (data not shown). It is expected that increases in GCase activity will be observed in other organs upon further treatment.

Figure 3:
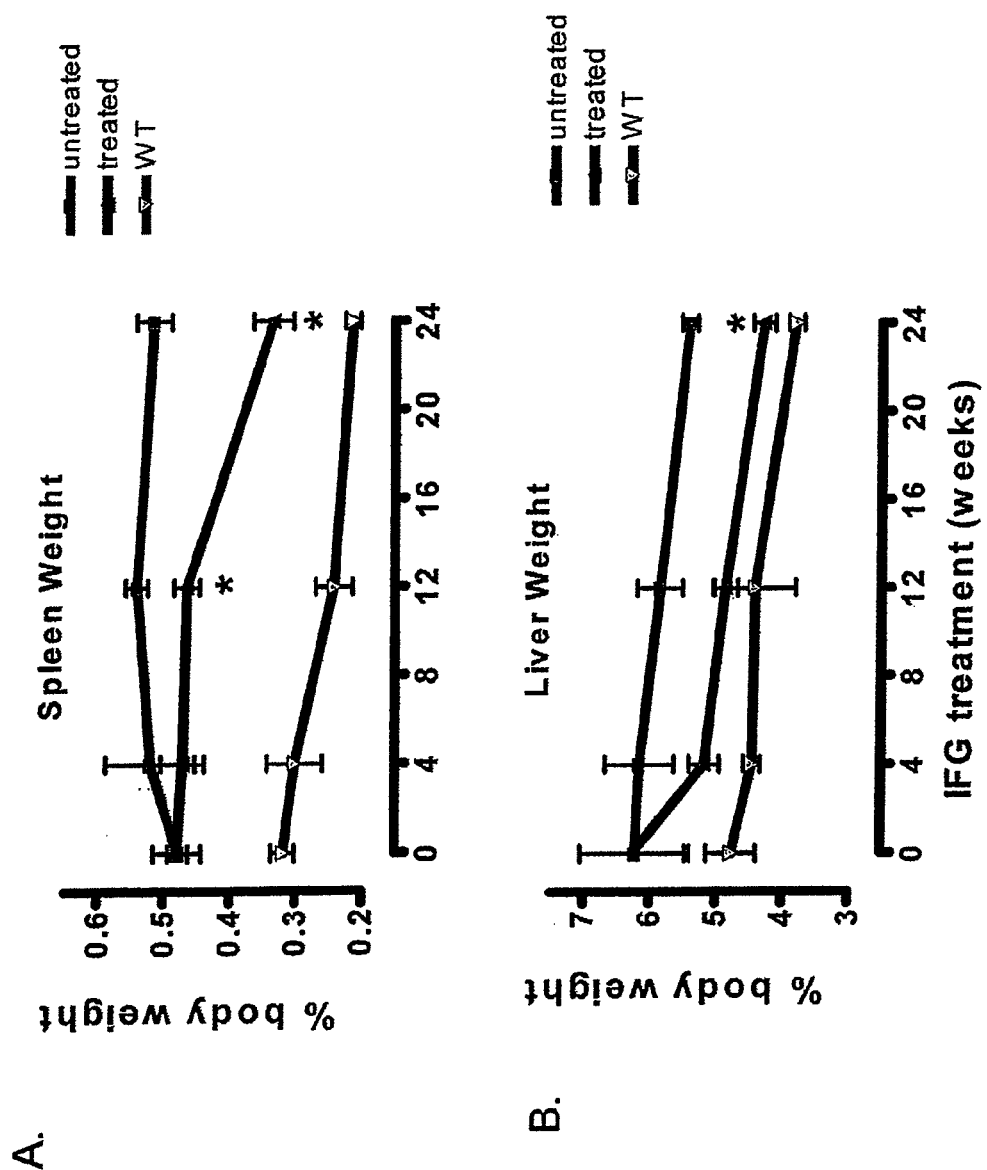
FIG. 3 depicts the effects of treatment with isofagomine on body tissue (spleen and liver, 3A-B, respectively) weights at over 2-24 weeks.

Body and Tissue Weight. After 12 weeks of isofagomine treatment, treated mice exhibited a body weight of about 33 g, intermediate between wild-type mice (about 40 g) and untreated mice (about 29 g) (data not shown). By contrast, spleen weight (FIG. 3A) was significantly decreased by 12 weeks of treatment in treated mice (0.09 mg) compared with untreated mice (0.11 mg). Wild-type spleens were about 0.08 mg. This persisted (reaching significance) after 12 weeks of treatment, where spleen weight was 0.12 mg in the treated mice compared with 0.15 mg in untreated mice and 0.10 mg in normal mice. Normalization of spleen weight is expected to continue for the duration of treatment.

Liver weight did not significantly change among treated, untreated and control wild-type mice after 12 weeks. (FIG. 3B), but achieved a significant reduction after 24 weeks (data not shown).

Figure 4:
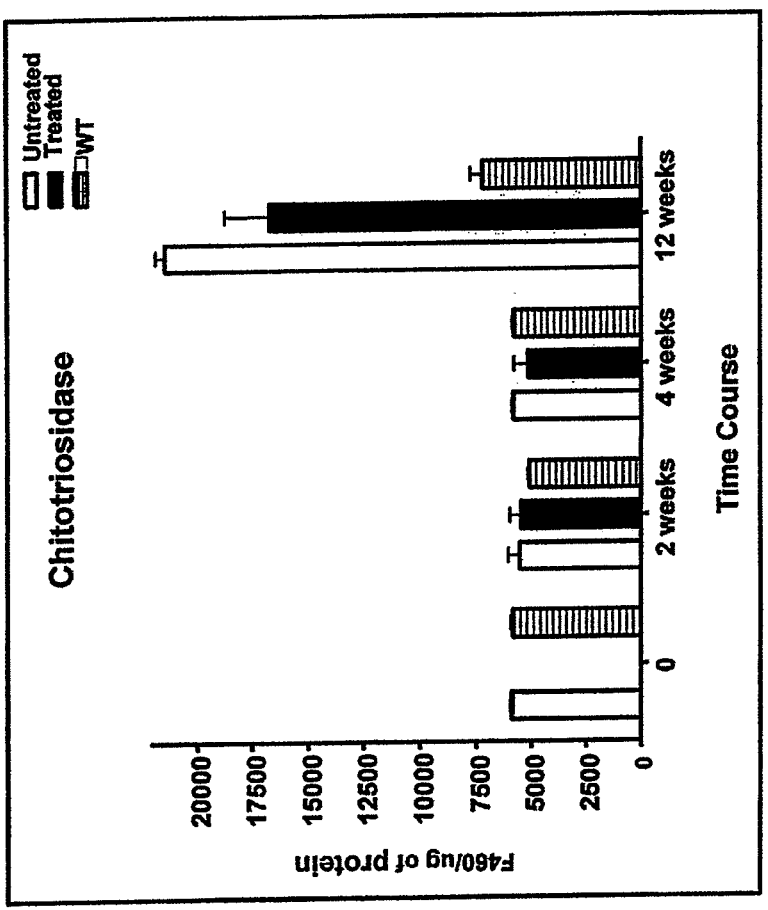
FIG. 4.

Chitotriosidase Activity. Although no difference in chitotriosidase levels were observed after 4 weeks of isofagomine treatment, levels were decreased after 12 weeks (about 17,000 μg of protein) compared with levels seen in untreated mice (>20,000 $F_{460}$ μg of protein) (p=0.1) (FIG. 4). However, levels were still elevated compared to wild-type mice (which had about 7500 μg of protein). Again, continued decrease in chitotriosidase levels is expected with continued treatment.

Figure 5:
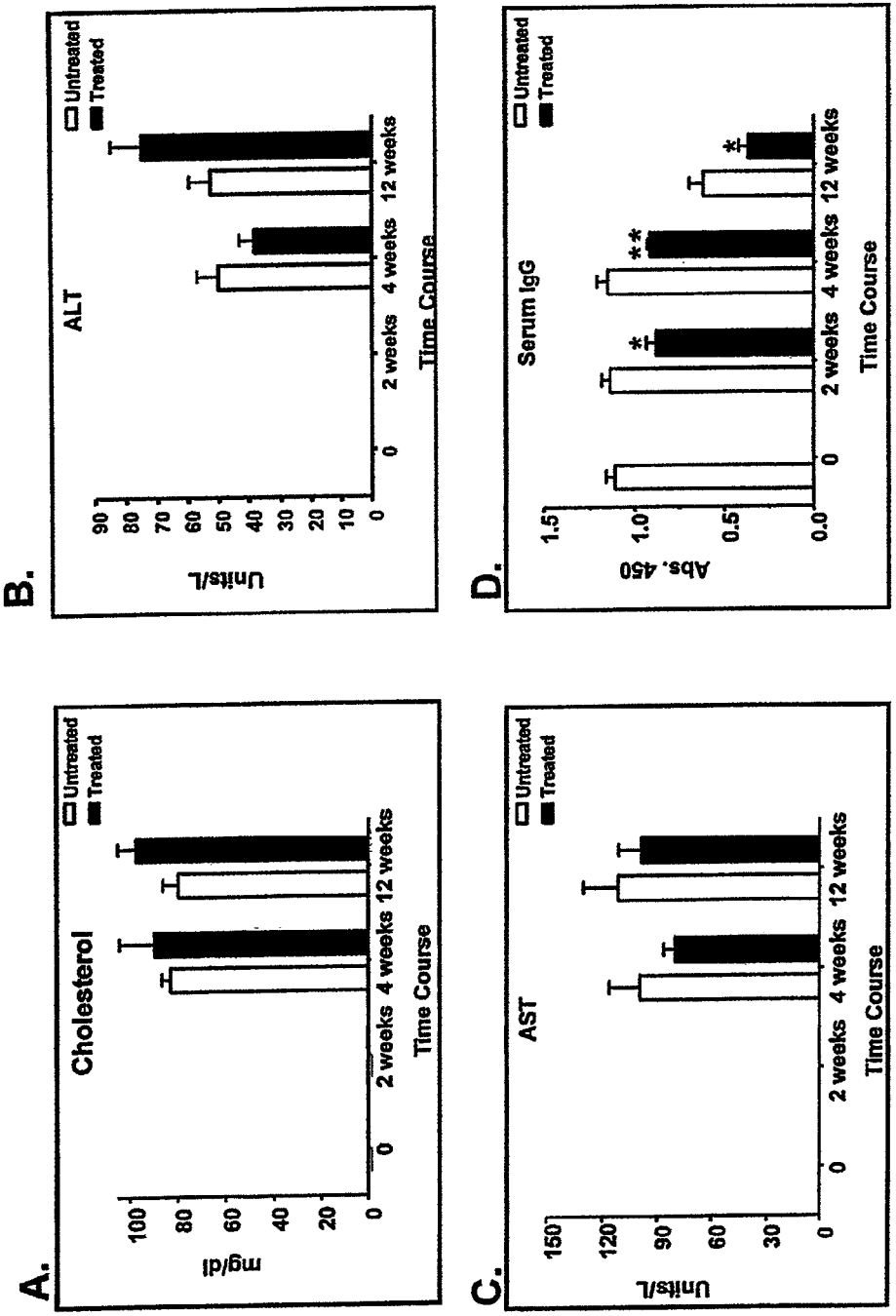
FIG. 5 shows serum parameters for cholesterol (5A), liver enzymes ALT (5B) and AST (5C) and IgG (5D) following treatment with IFG for 2, 4 and 12 weeks.

IgG, cholesterol, and liver enzymes. There were no significant differences in cholesterol, or liver aminotransferases (aspartate aminotransferase (AST) or alanine aminotransferase (ALT)) in isofagomine-treated versus untreated mice at 4 or 12 weeks (FIG. 5B-D, respectively)). By contrast, serum IgG levels showed significant decrease by 2 weeks of treatment, which persisted to 4 and 12 weeks of treatment, compared with untreated mice (FIG. 5A). This is significant improvement over treatment with recombinant GCase during enzyme replacement therapy. According to the manufacturer, 15% of patients develop IgG against the recombinant enzyme, 46% of whom also develop hypersensitivity reactions as a result.

Washout. Similar to above, after 4 weeks of treatment at 10 mg/kg/day, GCase activity was significantly elevated in liver, spleen, lung and brain in the L444P transgenic mice. Similarly, IgG was significantly decreased.

Example 3

IFG Increases Levels of Glucocerebrosidase, Inflammatory Cytokines, and Bone Metabolism in Gaucher Patient-Derived Cells To evaluate the effects of IFG on mutant GCase levels, an ex vivo response study with macrophages and EBV-transformed lymphoblasts derived from peripheral leukocytes of 60 patients was conducted. Plasma was also screened for potential biomarkers associated with inflammation, bone metabolism, and multiple myeloma. The study was conducted at eight sites in the United States.

Results

The study included 21 males with type I Gaucher disease, 1 male with type III Gaucher disease, and 18 females with type I Gaucher disease. Patients ranged in age from 7 to 83 years, and 38 of 40 patients were on enzyme replacement therapy (ERT). Macrophages were successfully derived from 34 of 40 patients, of which 32 demonstrated a dose-dependent increase in GCase levels (average=2.8-fold) when treated with IFG tartrate (5 days). Similar results were observed for 5 additional patient-derived lymphoblast cell lines. IFG significantly increased GCase levels in cells from patients with different genotypes including N370S/N370S (11), N370S/L444P (8), N370S/84insG (11), N370S/R163X, N370S/Y212H, L444P/del 136T, L444P/F216Y, L444P/L174F, G202R/R463C, and K79N/complex B exon 9/10 (type III GD). Maximum enhancement of GCase in macrophages was achieved at about 30 μM of IFG.

TRACP 5b, a marker of osteoclast activity, was elevated in the plasma of Gaucher subjects, especially in males, even those patients who were on ERT. Concurrently, the activity of bone-specific alkaline phosphatase (BAP) was reduced in the plasma of Gaucher subjects (especially females). This suggests that bone resorption may be favored over bone deposition in Gaucher patients, possibly contributing to the bone disease.

Other proinflammatory cytokines and chemokines also were elevated in some Gaucher subjects. These included IL-8, IL-17, VEGF, PARC, and MIP-1α. This combination of cytokines also has been associated with bone resorption and multiple myeloma (especially IL-17, VEGF, and MIP-1α). This is interesting in view of the fact that Gaucher patients, untreated or treated with ERT, have an elevated risk for developing multiple myeloma. Plasma levels of anti-inflammatory cytokines (IL-1ra, IL-2, IL-4, IL-5 IL-10, IL-13) were not elevated in Gaucher subjects.

Example 4

Identification of a Surrogate Marker in the Plasma of Gaucher Patients

Recently, a link between mutations in lysosomal enzymes and neurological disorders other than LSDs has been established. As one example, there is a well-established link between mutations in the Gba gene and parkinsonism and Parkinson's disease. In one study, a group of 17 patients with rare, early onset, treatment-resistant parkinsonism were found to have at least one allele with a Gba missense mutation, including homozygous and heterozygous individuals for N370S, a mutation typically associated with type 1, non-neuronopathic disease (Tayebi et al., *Mol. Genet. Metab.* 2003; 79; 104-109). In another study, a population of 99 Ashkenazi Jews with idiopathic Parkinson's disease were evaluated for six Gba mutations (N370S, L444P, 84GG, V394L, and R496H). Thirty-one Parkinson's patients had one or two mutant Gba alleles: 23 were heterozygous for N370S; 3 were homozygous for N370S; 4 were heterozygous for 84GG; and 1 was heterozygous for R496H (Aharon-Peretz et al., *New Eng. J. Med.* 2004; 351: 1972-77). The frequency of a mutant N370S allele was 5 times that among 1573 normal subjects, and that of 84GG was 21 times that of normal subjects. Among patients with Parkinson's disease, patients carrying a Gba mutation also were younger than those who were not carriers. This study suggests that heterozygosity for a Gba mutation may predispose Ashkenazi Jews to Parkinson's disease.

Parkinson's and Gaucher diseases also share some pathological features, including neuronal loss, astrogliosis, and the presence of cytotoxic Lewy-body-like α-synuclein inclusions in hippocampal neurons (the CA2-4 region). A recent publication described the extent of neurological pathology in all three forms of Gaucher disease (Wong et al., *Mol. Genet. Metabol.* 2004; 38: 192-207). Abnormalities in cerebral cortical layers 3 and 5, hippocampal CA2-4, and layer 4b were found in Gaucher patients having all three types. Neuronal loss was evident only in patients with types 2 and 3, whereas type 1 patients presented with astrogliosis (Wong et al., supra). Two patients with type 1 Gaucher and parkinsonism/dementia exhibited α-synuclein positive inclusions in hippocampal CA2-4 neurons, one patient had brainstem-type and cortical-type Lewy bodies, and one had marked neuronal loss of substantia nigra neurons (Wong et al., supra). In summary, all 4 patients with parkinsonism and dementia had hippocampal CA2-4 gliosis, and neuronal depletion, gliosis, and brainstem-type Lewy bodies in the substantia nigra.

Plasma levels of α-synuclein, when measure by ELISA, are elevated in Parkinson's patients compared to healthy controls (Lee et al. *J Neural Transm.* 2006; 113(10):1435-9). ( ). To determine whether α-synuclein was elevated in plasma from patients with Gaucher disease, for use as a biomarker to monitor the progress of treatment with chaperone therapy, ERT, SRT or other treatments, plasma α-synuclein levels were measured in 40 patients with Gaucher disease and compared with levels in plasma from 12 healthy volunteers.

Methods

Patient samples. Patient plasma samples were obtained as described above in Example 3.

ELISA. α-synuclein levels were determined. using a commercially available ELISA kit (BioSource International, Camarillo, Calif.) according to the manufactures instructions. Briefly, the ELISA plate was coated by overnight incubation with 1 µg/mL of nonbiotinylated mAb 211 (100 µL/well; Santa Cruz Biotechnology, Santa Cruz, Calif.), in 200 mM NaHCO3 (Sigma, St. Louis, Mo., USA), pH 9.6, containing 0.02% (w/v) sodium azide at 4° C., washed 4 times with PBST (PBS containing 0.05% Tween 20), and incubated with 200 µL/well of blocking buffer (PBS containing 2.5% gelatin and 0.05% Tween 20) for 2 h at 37° C. The plate was washed 4 times with PBST, and 100 µL of the samples to be tested were added to each well (neat). The plate was incubated at 37° C. for 2 h. After washing 4 times with PBST, 100 µL of biotinylated mAb 211 diluted to 1 µg/mL in blocking buffer was added, and incubated at 37° C. for 2 h. The wells were washed 4 times with PBST and incubated with 100 µL/well of ExtrAvidin-Alkaline phosphatase (Sigma) diluted 3:5000 in blocking buffer and incubated for 1 h at 37° C. The wells were then washed 4 times with PBST, before adding the enzyme substrate Yellow "pNPP" (Sigma) (100 µL/well) and leaving the color to develop for 30 min at room temperature. Absorbance values at 405 nm were determined and results were compared using an unpaired two tailed t-test.

Results

Figure 6:
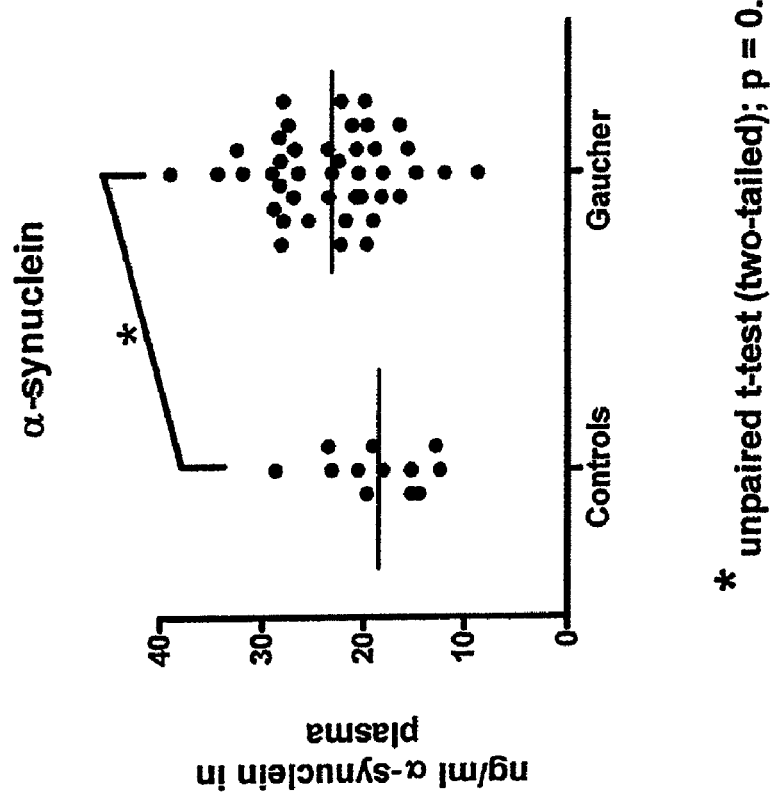
FIG. 6.

Compared to the healthy volunteer controls, α-synuclein levels were significantly elevated in plasma from the Gaucher patients (p=0.019; FIG. 6). The variances between the populations were not significantly different.

Accordingly, plasma α-synuclein can be used as a prognostic marker to evaluate treatment for Gaucher disease.

Example 5

Restoration of Disrupted Lysosomal Trafficking in Gaucher Fibroblasts

Although N370S Gaucher fibroblasts (from a human patient) do not demonstrate an accumulation of substrate (i.e., GluCer) in the cytoplasm, these fibroblasts exhibit abnormal lysosomal protein and GCase staining compared with wild-type fibroblasts. Treatment of N370S fibroblasts with SPC isofagomine increased the amount of GCase seen in the lysosome and restored a normal lysosomal staining pattern to the cells.

Methods

Cell culture. N370S fibroblasts (DMN89.15) were cultured in DMEM with 10% FBS and 1% penn/strep at 37 C with 5% $CO_2$. Wild-type fibroblast cell line CRL-2097 form a healthy individual was used as a control. Cells were subcultured from 10 cm plates into 12-well plates with cover slips. Cells from one confluent 10 cm plate were diluted in 38 ml of culture medium. Isofagomine or C-benzyl-isofagomine was added from a 10 mM stock solution (5% DMSO) to each well of a 12-well plate at the following concentrations:

C-benzyl-isofagomine-control (secondary antibody only); untreated; 0.03 µM; 0.1 µM; 0.3 µM; 1.0 µM; 3.0 µM; and 10.0 µM.

Isofagomine-control (secondary antibody only); untreated; 10 µM; 30 µM; 100 µM; 1 nM; 3 nM; and 10 nM.

Cells were cultured for a total of about 6 days.

Fixing and Staining. Cells were washed for 5 minutes in PBS, fixed for 15 minutes in 3.7% paraformaldehyde (in PBS), washed again for 5 minutes in PBS, and permeabilized with 0.5% saponin for 5 minutes. Cells were then washed with PBS containing 0.1% saponin, treated for 5 minutes with fresh 0.1% sodium borohydride/0.01% saponin, and washed 3 times with PBS with 0.1% saponin/1% BSA for 5 minutes each.

Cells were incubated for 1 h with 500 µl of primary anti-GCase (1:200) or anti-LAMP-1 (1:200; BD Pharmingen, Cat. No. 555798) antibody solution in PBS with 1% BSA. Lysosomal staining using LysoTracker® Red (Cambrex, East Rutherford, N.J.) was performed according to the manufacturer's instructions. Following incubation, cells were washed 3 times in 1% BSA containing 0.1% saponin in PBS, followed by incubation with the secondary antibody solution (1:500; anti-rabbit AlexaFluor588 for anti-GCase and anti-mouse IgG AlexaFluor594 for anti-LAMP-1). Cells were mounted onto coverslips, sealed, and immediately viewed.

Confocal Microscopy. Cells were visualized using a confocal microscope. The red and green channel gains were set to 6 and the laser power was optimized using the intensity window, and were not adjusted for the rest of the experiment. All slides were analyzed at the same sitting and all images were gathered without any zoom using the 20× and 60× lens, the small pinhole, optimal pixel size, an average of 2 scans, and red and green channels were acquired simultaneously as in all previous experiments.

All images were displayed at the same intensity and red+ green channel intensity graphs were generated for each image by placing the cursor over the maximum number of cells.

Future measurements can be made by calculating a ratio for overlapping red (LAMP-1) and green (GCASE) pixels.

Results

Figure 7:
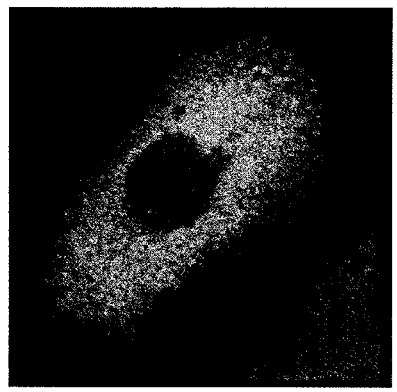
FIG. 7 depicts fluorescent staining of lysosomes using LysoTracker Red in cells from Gaucher fibroblasts (7A) and normal fibroblasts (7B). Staining for lysosomal protein LAMP-1 was also performed on normal fibroblasts (7C) and Gaucher fibroblasts (7D).
Figure 7:
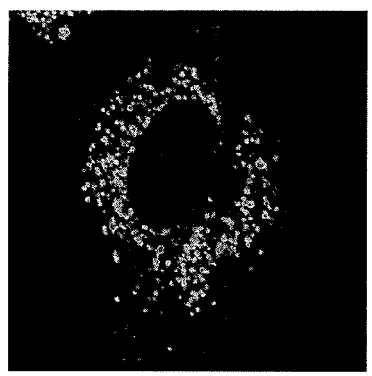
Figure 7:
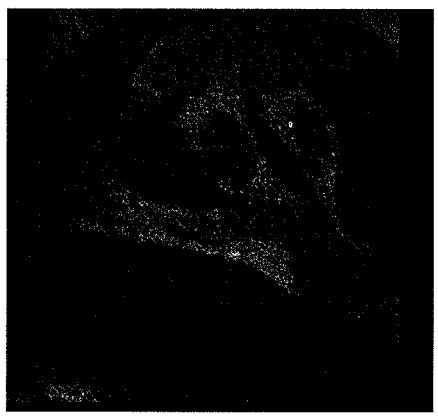
Figure 7:
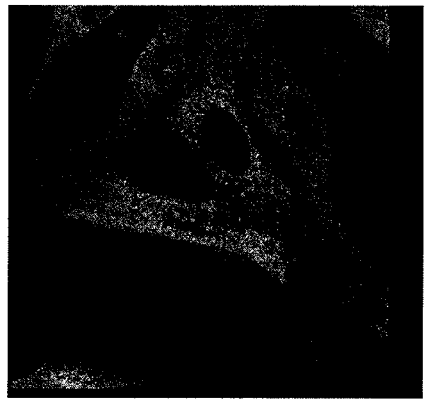
Figure 7:
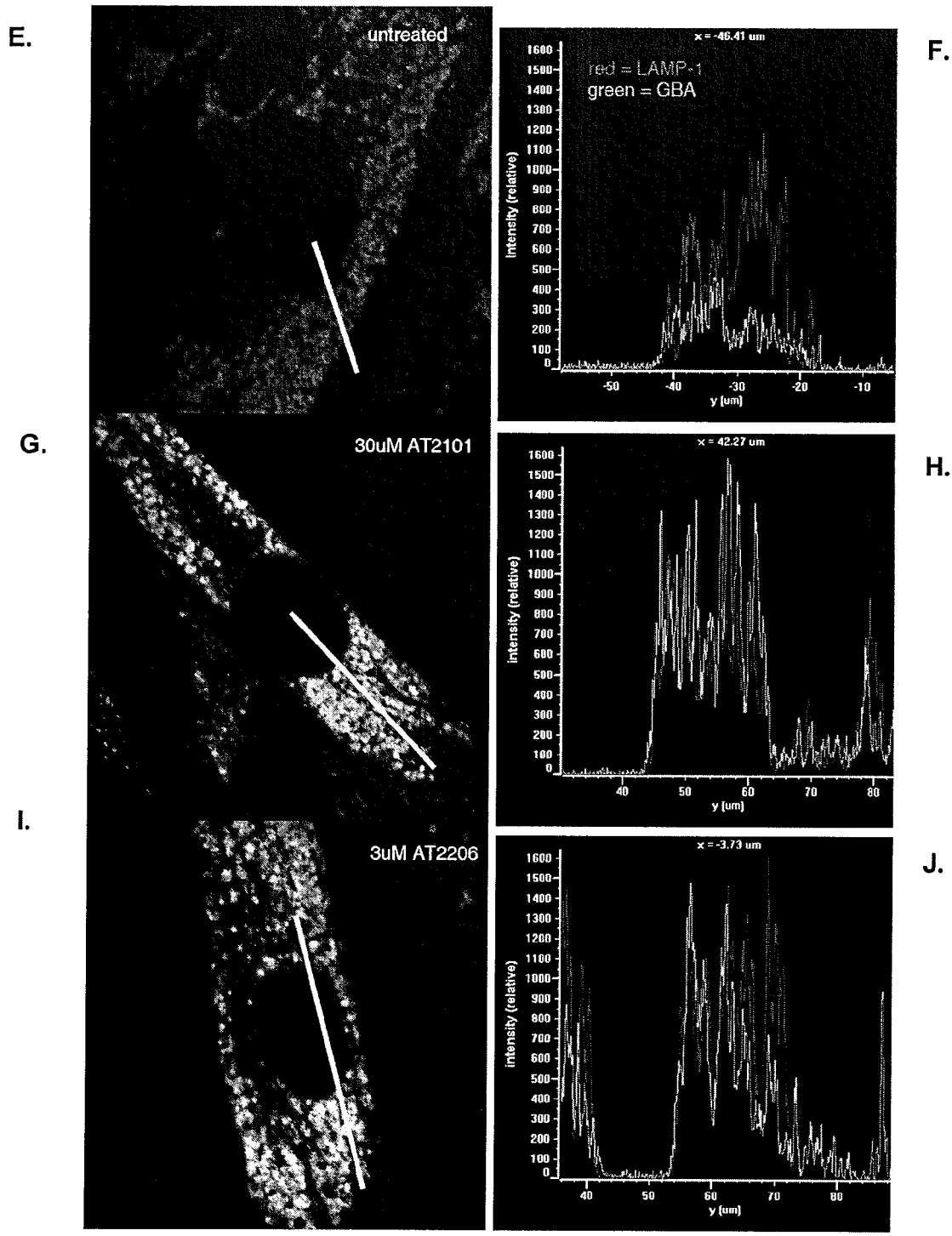
Figure 7:
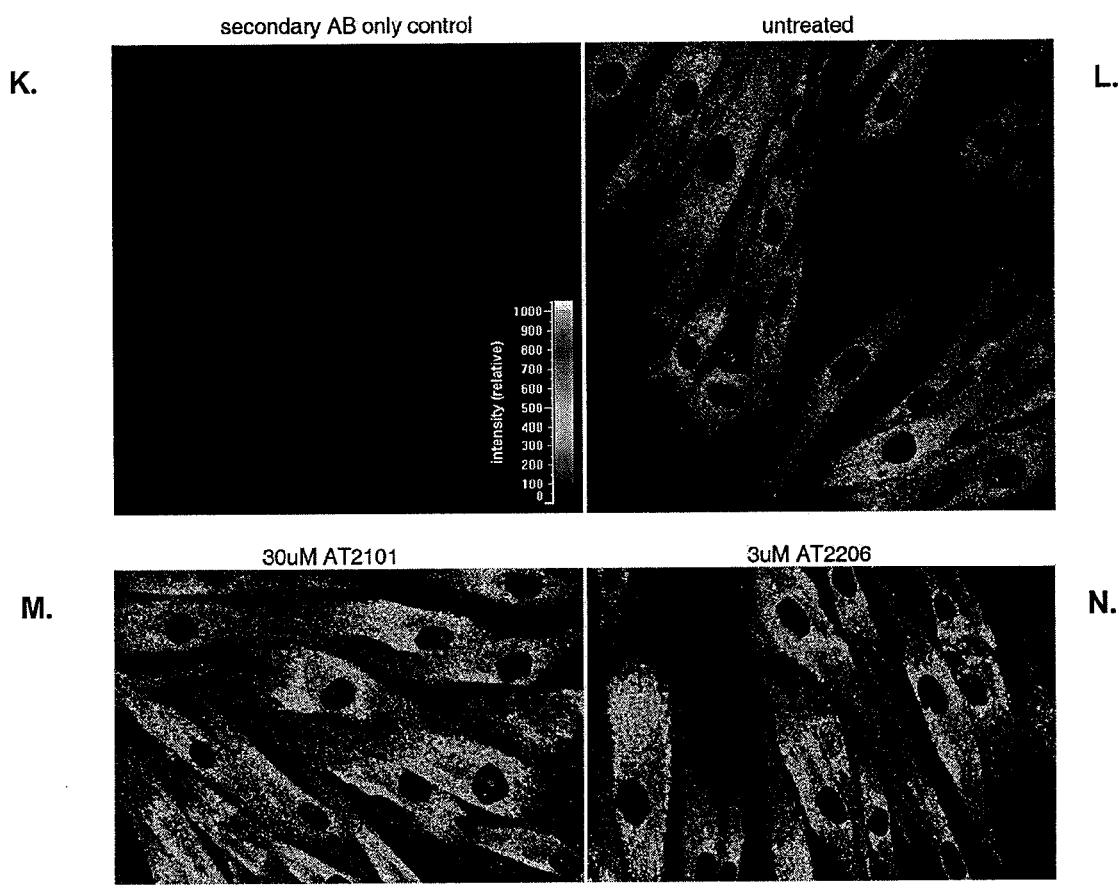

Gaucher N370S fibroblasts that have been confluent for more than 5 days exhibit a granular lysosomal staining pattern using LysoTracker® Red (FIG. 7A) compared with a normal fibroblast, which has a punctuate staining pattern (FIG. 7B). Similar results were shown for L444P fibroblasts (data not shown). Staining for lysosomal LAMP-1 is shown in both N370S and normal fibroblasts (FIGS. 7C-D, respectively). More LAMP-1 is shown in Gaucher fibroblasts.

Treatment with 30.0 µM isofagomine (FIG. 7G-H) and 3.0 µl C-benzyl-isofagomine (FIG. 7I-J) increased the amount of GCase in the lysosomes and re-established a normal lysosome punctuate staining pattern for GCase and LAMP-1 compared with an untreated control (FIG. 7E-F), as indicated by dual staining.

FIGS. 7K-N shows changes in GCase lysosomal staining in N370S Gaucher fibroblasts as follows: (K)—control (secondary antibody only); (L)—untreated N370S fibroblasts; (M)—30 µM isofagomine; and (N) 3 µM C-benzyl-isofagomine. GCase staining is shown to localize to lysosomes in chaperone-treated versus untreated controls. Similar results were obtained for L444P Gaucher fibroblasts (data not shown).

These results establish that treatment with pharmacological chaperones increases GCase levels in the lysosome. In addition to increased trafficking of the lysosome, pulse-chase experiments demonstrated that IFG increases N370S GCase in the ER (data not shown).

This improvement in normal cell morphology with chaperone treatment is due to a decrease in the amount or accumulation of mutant GCase, possibly in the form of aggregates, in the ER and/or cytosol. Since it has been demonstrated that the SPCs evaluated cross the blood-brain barrier, this strategy could relieve CNS symptoms Gaucher patients with neuronopathic Gaucher disease (Types 2 and 3).

Example 6

Increase of Polyubiquinated Proteins with Chaperone Treatment in Gaucher Fibroblasts; Restoration of the Proteasome Degradation Pathway Anti-polyubiquitinated protein (PUP) and anti-GCase labeling of healthy human fibroblast was compared with that in fibroblasts from a Gaucher patient having the L444P Gba mutation, and Gaucher patient fibroblasts having the N370S Gba mutation.

Methods

Cell culture. L444P Gaucher fibroblasts (cell line GM10915); N370S Gaucher fibroblasts (cell line DMN89.15); and fibroblasts from a healthy individual (CRL-2097) were cultured in DMEM with 10% FBS and 1% PS at 37 C with 5% $CO_2$. Cells were sub-cultured from 10 cm plates into 12-well plates with sterile cover slips. N370S cells from one confluent T-75 flask were diluted 1:6 and cultured for another 4 days.

Chaperones isofagomine or C-benzyl-isofagomine was added from a 10 mM stock solution (5% DMSO) to each row of a 12-well plate at the following concentrations:

C-benzyl-isofagomine: untreated; control (secondary antibody only); 0.03 µM; 0.1 µM; 0.3 µM; 1.0 µM; 3.0 µM; and 10.0 µM.

Isofagomine: untreated; control (secondary antibody only); 10 µM; 30 µM; 100 µM; 1 nM; 3 nM; and 10 nM.

Fixing and staining. Cells were washed once in PBS for 5 minutes, followed by fixation for 15 minutes in fresh 3.7% paraformaldehyde. Cells were then washed once in PBS for 5 minutes, followed by permeabilization for 5 minutes in 0.2% Triton X-100. Cells were then washed again in PBS for 5 minutes and treated for 5-10 minutes with fresh 0.1% sodium borohydride. Cells were washed three times in PBS with 1% BSA (5 min each) prior to staining.

Cells were next incubated for 1 hour with 500 µl of the following primary antibodies (diluted 1:200 in PBS with 1% BSA):
  1. Mouse monoclonal antibody to ubiquitinated proteins clone FK1 (AFFINITI® Research Products Cat. No. PW 8805)
  2. Rabbit anti-GCase antibody Cells were then washed three times with PBS with 1% BSA, followed by incubation for 1 hour with a 1:500 dilution of the following secondary antibodies:
  1. Goat Anti-Mouse IgM (µ chain) AlexaFluor568 (Molecular Probes Cat. No. A21043);
  2. Goat Anti-Rabbit IgG (H+L) highly cross absorbed AlexaFluor488 (Molecular Probes Cat. No. A11034)

Cells were washed three times in PBS with BSA, mounted, and stored at 4° C. prior to visualization.

Results

Initial experiments indicated that the concentration of polyubiquitinated proteins (PUP) in cells is greater (very intense) in healthy cells than in Gaucher N370S and L444P fibroblasts (much less intense). In addition, treatment of Gaucher fibroblasts with specific chemical chaperones increases the PUP staining in the Gaucher cells. As stated above, this is likely because protein aggregation is known to inhibit the ubiquitin/proteasome pathway. Accordingly, decreasing aggregation using chaperones may re-start the proteasome-mediated degradation pathway.

Example 7

Analysis of Surrogate Markers in Human Gaucher Patients and Human Controls

This study included 26 males with type I GD, 6 males with type III GD, 26 females with type I GD and 5 females with type III GD representing 19 different genotypes. Patients ranged in age from 4 to 83 years; 59 of 63 patients were receiving enzyme replacement therapy and blood was drawn immediately prior to enzyme infusion.

Figure 8:
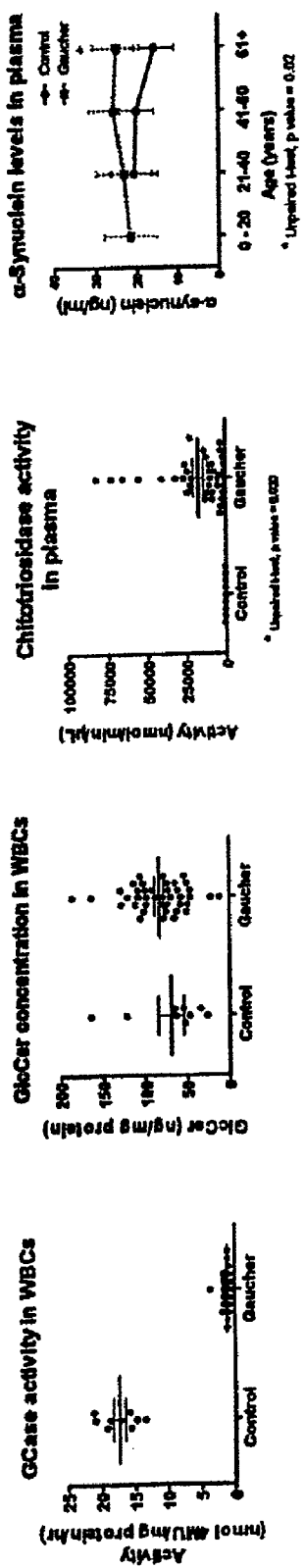
FIG. 8.
Figure 9:
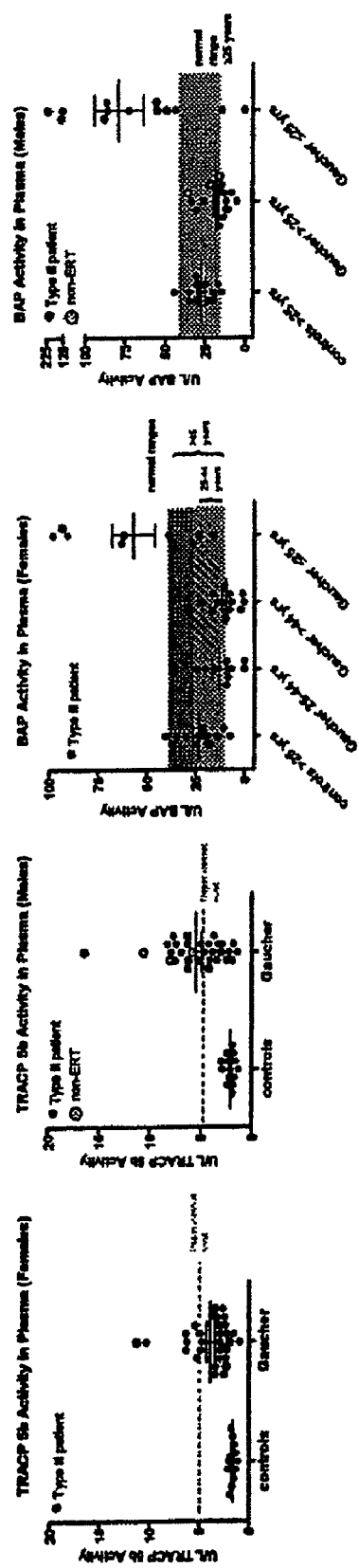
FIG. 9.
Figure 10:
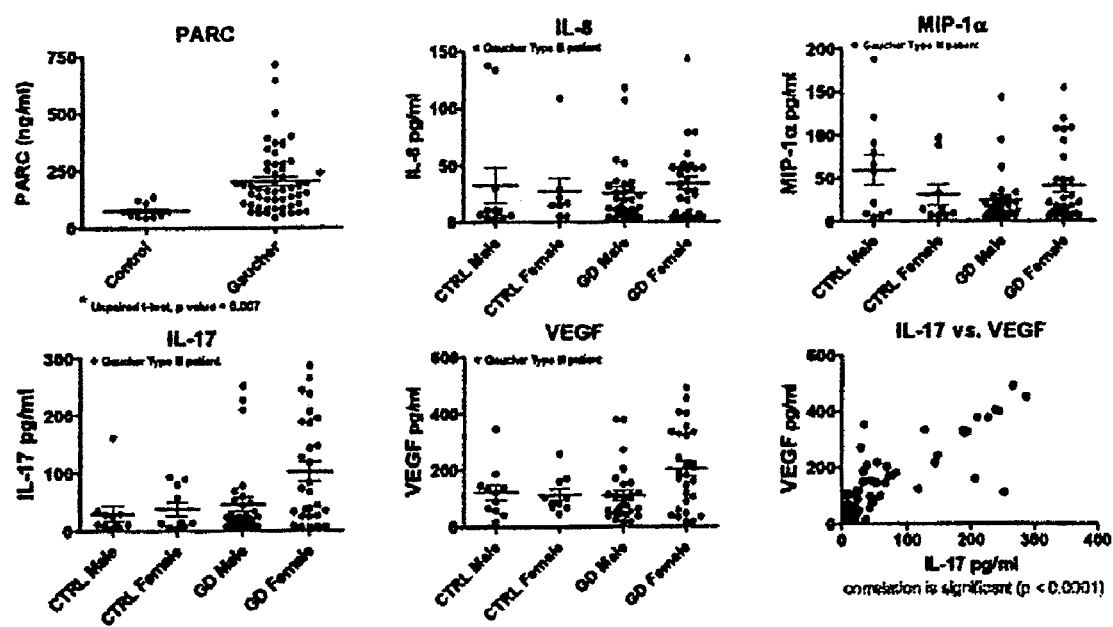
FIG. 10.

Analysis of untreated WBCs yielded reduced GCase activity compared to controls, normal GlcCer levels (most patients were receiving ERT), and elevated chitotriosidase activity (FIG. 8). Since multiple studies have identified mutations in Gba, the gene that encodes for GCase, as a potential risk factor for synucleinopathies, we screened for plasma levels of α-synuclein. Surprisingly, GD patients showed elevated levels of total α-synuclein compared to controls (FIG. 8). Interestingly, we have also found that α-synuclein accumulation correlates with the accumulation of glucosylceramide of mouse models with significantly reduced GCase activity. Markers of osteoclast (TRACP 5b) and osteoblast (BAP) activities were abnormal for most patients. In general, TRACP 5b activity was elevated in many patients while BAP levels were lower than normal (FIG. 9). These results suggest that bone metabolism is altered in most patients, favoring osteoclast activity and bone resorption. Interestingly, proinflammatory cytokines and chemokines PARC(CCL18), IL-8, IL-17, VEGF and MIP-1α were elevated in some patients compared to controls, and a significant correlation ($p<0.0001$) was observed for IL-17 and VEGF levels (FIG. 10). IL-17 is produced exclusively by CD4+ memory T-Cells and can induce the production of VEGF by other cells. These cytokines can promote osteoclastogenesis and osteoclast survival and have also been implicated in the pathogenesis of multiple myeloma, which may be relevant to GD since it has been reported that Gaucher patients have an increased risk for developing multiple myeloma.

We also screened patients for DKK1 and found them to be lower in most Gaucher patients relative to age-matched controls (data no shown). Plasma levels of other proinflammatory (IL-1 [α, β], IL-6, IL-7, IL-12p40, IL-12p70, IL-15, IL-17, fractalkine, EGF, TGFα, sCD40L, GM-CSF, eotaxin, sCD14, IP-10, IFN-v, G-CSF, MIP-1β, TNFα, HSP60, HSP70), anti-inflammatory (IL-1ra, IL-2, IL-4, IL-5, IL-10, IL-13) and cardiovascular (CRP, SAA, SAP) markers were unremarkable for most GD patients when compared to controls (data not shown).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. An ex vivo method for monitoring a patient with Gaucher disease under treatment, which comprises determining whether there is an improvement of a surrogate marker that is associated with Gaucher disease following administration of a specific pharmacological chaperone of acid β-glucosidase wherein the surrogate marker is bone-specific alkaline phosphatase (BAP) and wherein a sample derived from the patient is used to assay the surrogate marker wherein an improvement of the surrogate marker indicates that the patient is responding to treatment with the specific pharmacological chaperone.

2. The method of claim 1, wherein the specific pharmacological chaperone is isofagomine.

3. The method of claim 1 wherein the pharmacological chaperone results in an increase of acid β-glucosidase activity of at least 2-fold.

4. The method of claim 1, wherein the patient has Type 2 or 3 Gaucher disease.

* * * * *